(12) United States Patent
Chang

(10) Patent No.: US 8,835,615 B2
(45) Date of Patent: Sep. 16, 2014

(54) 2'-FLUORINE-4'-SUBSTITUTED-NUCLEOSIDE ANALOGUES, PREPARATION METHODS AND USES THEREOF

(76) Inventor: Junbiao Chang, Zhengzhou (CN)

( * ) Notice: Subject to any disclaimer, the term of this patent is extended or adjusted under 35 U.S.C. 154(b) by 163 days.

(21) Appl. No.: 12/669,342

(22) PCT Filed: Jun. 27, 2008

(86) PCT No.: PCT/CN2008/001239
§ 371 (c)(1),
(2), (4) Date: Apr. 28, 2010

(87) PCT Pub. No.: WO2009/009951
PCT Pub. Date: Jan. 22, 2009

(65) Prior Publication Data
US 2010/0234584 A1    Sep. 16, 2010

(30) Foreign Application Priority Data

Jul. 16, 2007  (CN) .......................... 2007 1 0054781
Aug. 7, 2007   (CN) .......................... 2007 1 0137548

(51) Int. Cl.
*C07H 19/00* (2006.01)
*C07H 19/14* (2006.01)
*C07H 19/16* (2006.01)
*C07H 19/06* (2006.01)

(52) U.S. Cl.
CPC ............... *C07H 19/06* (2013.01); *C07H 19/14* (2013.01); *C07H 19/16* (2013.01)
USPC ..................................................... 536/22.1

(58) Field of Classification Search
USPC ....................................................... 536/22.1
See application file for complete search history.

(56) References Cited

U.S. PATENT DOCUMENTS

2009/0318380 A1 * 12/2009 Sofia et al. ...................... 514/45

FOREIGN PATENT DOCUMENTS

| CN | 1712409 A | 12/2005 | |
|---|---|---|---|
| WO | WO 99-43691 | 9/1999 | |
| WO | WO 02-057287 | 7/2002 | |
| WO | WO 02/100415 A2 * | 12/2002 | ......... A61K 31/7068 |
| WO | WO 2005-003147 | 1/2005 | |
| WO | WO 2007/038507 | 4/2007 | |
| WO | WO 2008-043704 | 4/2008 | |

OTHER PUBLICATIONS

Klumpp et al., The Journal of Biological Chemistry, 2008, 283, pp. 2167-2175.*

By Jin et al., Arch. Pharm. Res., 1995, 18, 364-365.*
Yun-Ho, Jin, et. al., Arch. Pham. Res., vol. 18, No. 5, "Synthesis and Antiviral Activity of Fluoro Sugar Nucleosides 1: Studies on 4'-Azido-2'-Deoxy-2'-Fluoro-Arabinofura-nosyl Nucleosides," pp. 364-365, 1995.
Klumpp, Klaus, et. al., Journal of Biological Chemistry, vol. 283, No. 4, "2'-Deoxy-4'-azido Nucleoside Analogs Are Highly Potent Inhibitors of Hepatitis C Virus Replication Despite the Lack of 2'-α-Hydroxyl Groups," pp. 2167-2175, Jan. 25, 2008.
European Patent Office, Communication pursuant to Article 94(3) EPC, European Patent Application No. 06 825 120.6-2101, dated Jul. 26, 2012 (9 pages).
Response dated Nov. 22, 2012, European Patent Application No. 06825120.6-2101 (30 pages).
WO2007 038507 A3 publication page and International Search Report (2 pages).

* cited by examiner

*Primary Examiner* — Elli Peselev
(74) *Attorney, Agent, or Firm* — Workman Nydegger

(57) ABSTRACT

The present invention provides 2'-fluorine-4'-substituted-nucleoside analogs or their pro-drugs or 5'-phosphate esters (including the pro-drugs of the 5'-phosphate esters), preparation methods and uses thereof. The compounds have the general formula as follows:

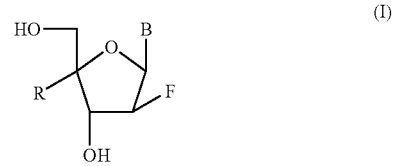

wherein:

B =

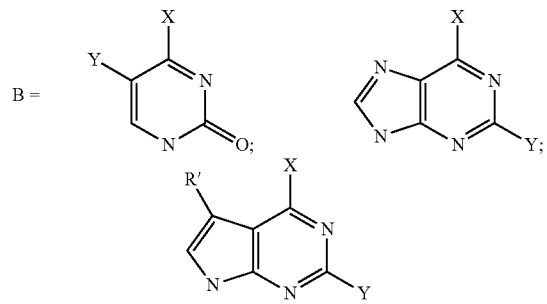

R = CH$_3$, CN, N$_3$, C≡CH;
R' = H, F;
X = F, OH, NH$_2$;
Y = H, CH$_3$, F, OH, NH$_2$

The compounds are used in the synthesis of drugs for the treatment of virus infection, especially for the treatment of HBV, HCV or HIV infection.

13 Claims, No Drawings

2'-FLUORINE-4'-SUBSTITUTED-NUCLEOSIDE ANALOGUES, PREPARATION METHODS AND USES THEREOF

CROSS-REFERENCE TO RELATED APPLICATIONS

This application is a National Stage entry of PCT/CN08/01239 filed on 27 Jun. 2008 and claims foreign priority to China application No. 200710054781.2 filed on 16 Jul. 2007 and China application No. 200710137548.0 filed on 7 Aug. 2007, the entireties of which are incorporated herein by reference.

FIELD OF THE INVENTION

This invention relates to nucleoside analogues, preparation methods and uses thereof, and more particularly, relates to 2'-fluorine-4' substituted nucleoside analogues, preparation methods and uses thereof.

BACKGROUND OF THE INVENTION

The first case of AIDS patient was discovered in the United States in 1981. It was until in 1983 that the AIDS virus (HIV) is isolated and identified by scientists, revealing that HIV composed of 9749 nucleotides only is categorized into the Lentivirinae in Retroviridae. At present, the replication cycle of HIV virus has been made generally clear. According to relevant research findings, the reproduction process of the HIV virus can be divided into the following steps: the viral adsorption, invasion and uncoating, the reverse transcription, the integration of virus as well as the synthesis, the assembly, the release and the maturing of viral RNA and protein. Each of these steps can be used as a target for screening the Anti-HIV drugs, and the protein synthesis and the viral genome DNA replication are the most critical steps. At present, the screening of anti-HIV drugs is focused on finding the inhibitors for these specific enzymes, including the reverse transcriptase (RT) inhibitors, the protein synthesis inhibitors and the reverse transcriptase initiation inhibitors. HIV-reverse transcriptase is a multifunctional enzyme, which also has the activities of RNA dependent DNA polymerase, DNA dependent DNA polymerase and RNase H. Initially, DNA chain (−) synthesis of HIV is processed with the virus genome RNA acting as a template and the host cell RNA as a primer, and then the synthesis of DNA chain (+) is completed in the same way. After the completion of the reverse transcription, all the genetic information carried by HIV is transformed from single-stranded RNA into double-stranded mDNA. Reverse transcriptase inhibitors can prevent the extension of mDNA and interfere with the HIV reverse transcription process, and thus become the drugs for the chemotherapy of AIDS. According to different mechanisms of the inhibitors, these drugs could be divided into two categories: 1) the nucleoside reverse transcriptase inhibitors which realize anti-HIV actions by being inserted into the viral DNA to promote the viral DNA to become defective DNA, resulting in the invalid duplication after integration of HIV with host cell during HIV DNA reverse transcription, and the available drugs include Zidovudine (AZT), Didanosine (ddI), Zalcitabine (ddC), Stavudine (d4T), Lamivudine (3TC), Abacavir; 2) non-nucleoside reverse transcriptase inhibitors, and mechanisms thereof are to prevent HIV RNA from being directly connected to the RT and thus being encoded into DNA. The available drugs include Nevirapine, Delavirdine and Efavirenz.

Zidovudine, the first commercial anti-HIV drug that was put into market in 1987, is a nucleoside reverse transcriptase inhibitor. This drug can alleviate the symptoms and prolong the lives of the patients, although it has much toxicity and failed to cure any patient. Later, several anti-HIV nucleoside analogue agents have also become available in the market. Therefore, nucleoside analogues are considered as an important class of compounds with anti-HIV activity. However, these drugs have some shortcomings at present. On the one hand, their effect is limited; on the other hand, severe toxic and side effects and drug resistance will be generated in a long-term administration. Accordingly, the synthesis of new nucleoside analogues is still an important trend in the research. In order to find more effective nucleoside anti-viral agents, diversified chemical modifications have been made for the nucleosides, including the fluorine-containing nucleoside analogues (Clark, J. PCT Patent Appl., WO 2005003174; Ismaili, H. M. A. PCT Patent Appl., WO 0160315A22001). Relevant studies have shown that these compounds have antiviral activity at different levels, and are a new type of compounds with anti-viral activities. However, in the currently available literatures, it is not found any relevant report on the synthesis of 2'-fluoro-4'-substituted-D- and L-nucleoside analogues of the present invention as well as on their applications in the preparation of anti-HIV, anti-HBV and anti-HCV drugs.

SUMMARY OF THE INVENTION

It is the primary object of the present invention to provide 2'-fluoro-4'-substituted nucleoside analogues. It is another object of the present invention to provide the synthesis method for such compounds. It is a further object of the present invention to provide the uses of such compounds in pharmacology.

To achieve the objects of the present invention, the technical solutions are provided as follows:

2'-fluoro-4'-substituted nucleoside analogues of the present invention has the structure of the general formula (I):

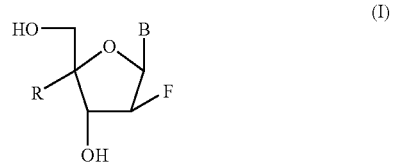

wherein:

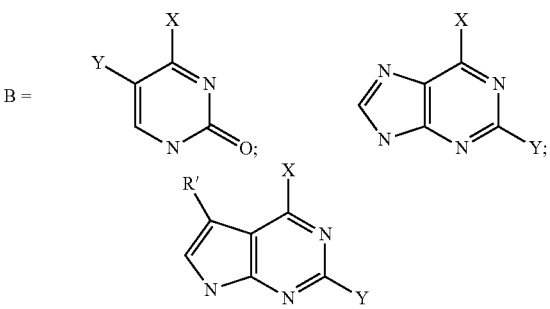

R = CH$_3$, CN, N$_3$, C≡CH;
R' = H, F;
X = F, OH, NH$_2$;
Y = H, CH$_3$, F, OH, NH$_2$.

The above compounds may exist in the form of salts, which are generated through the reaction between the active compounds (I) or their pro-drugs or their 5'-phosphate esters and organic or inorganic acid.

The above compounds may be one of the following compounds, but are not limited to these compounds:
1
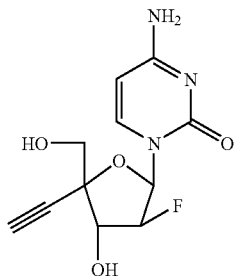
2
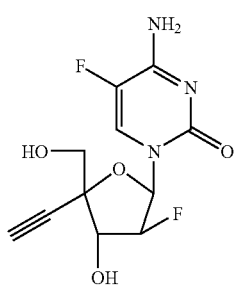
3
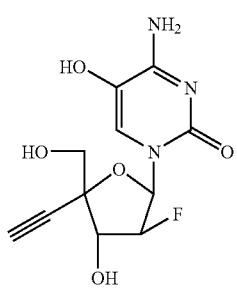
4
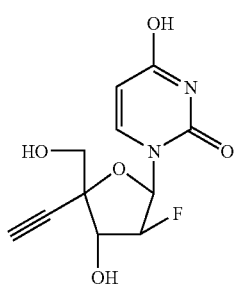
5
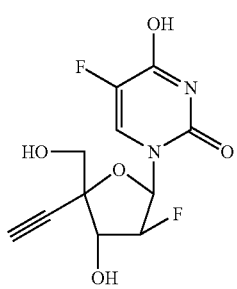
-continued
6
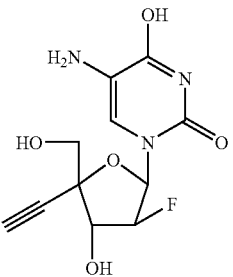
7
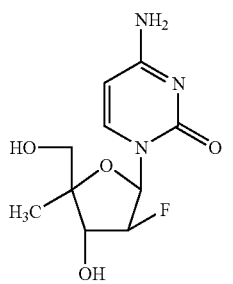
8
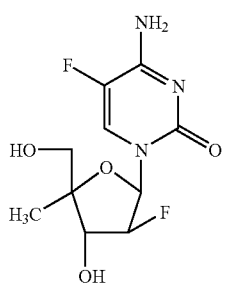
9
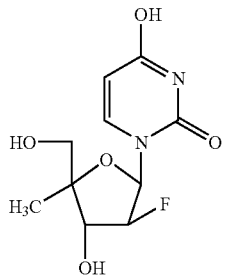
10
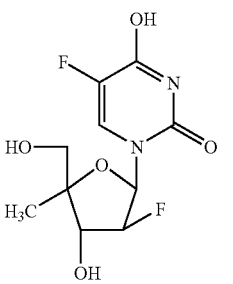

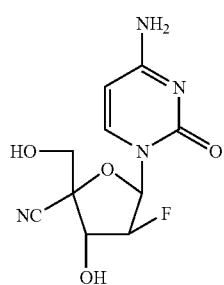
11
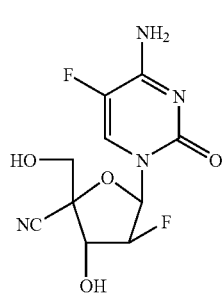
12
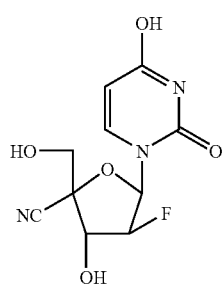
13
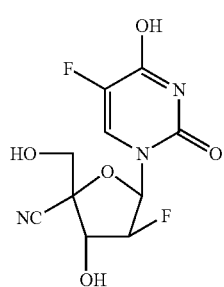
14
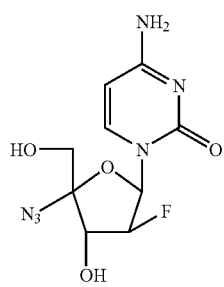
15
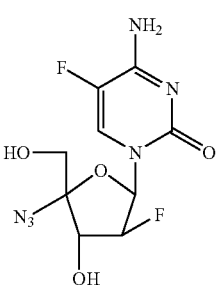
16
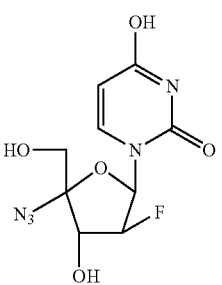
17
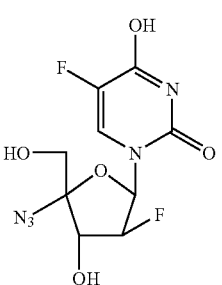
18
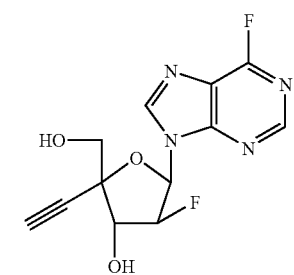
19
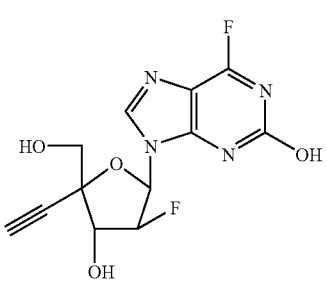
20

21
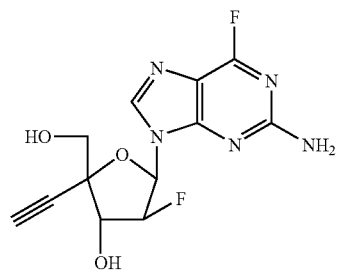
22
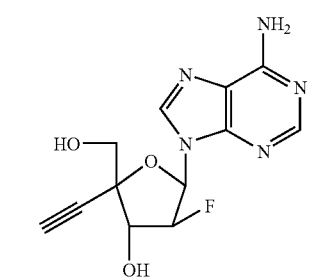
23
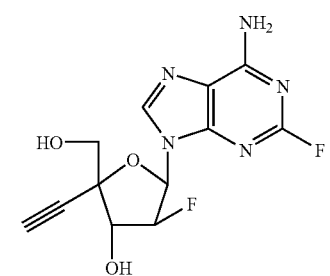
24
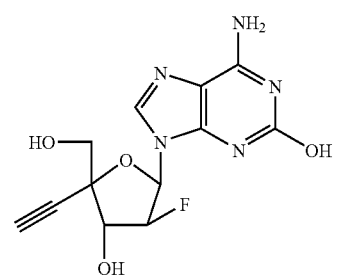
25
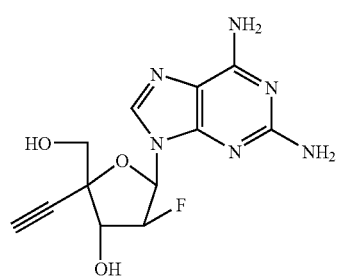
26
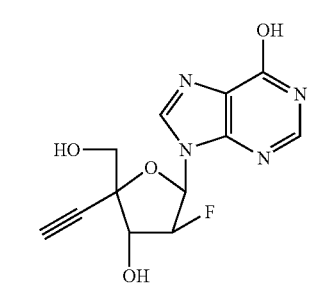
27
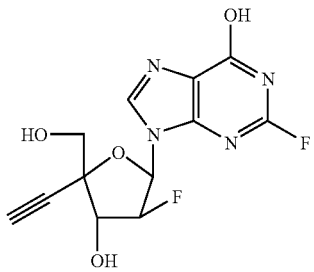
28
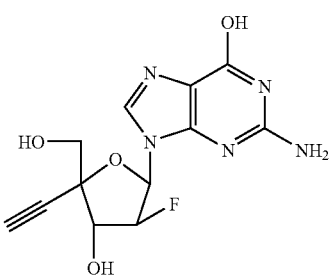
29
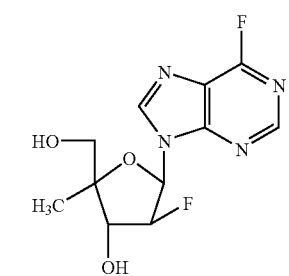
30
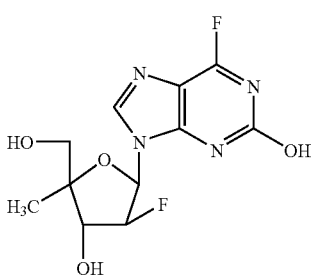
31
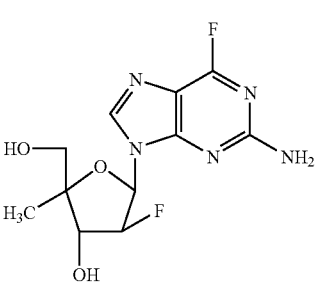
32
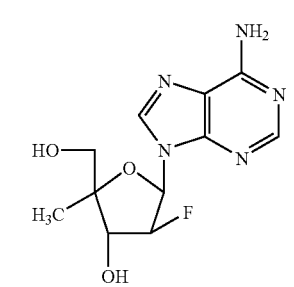

33
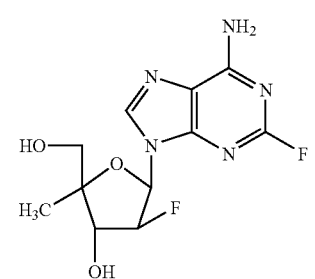
34
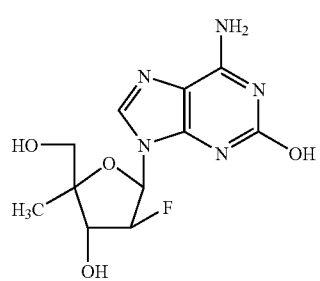
35
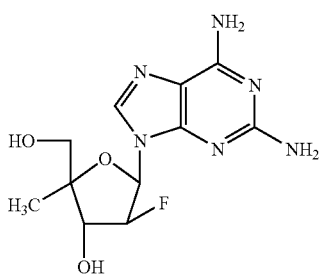
36
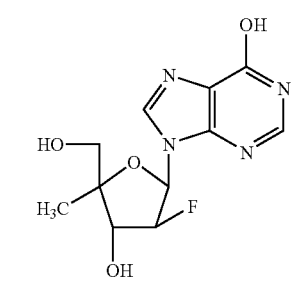
37
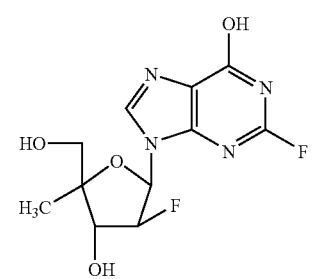
38
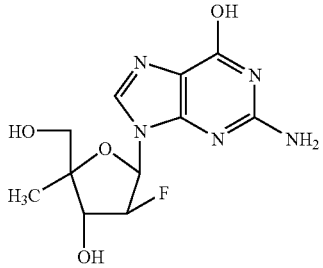
39
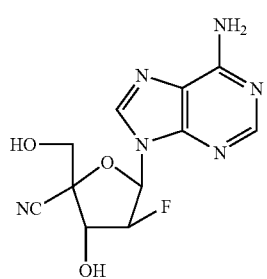
40
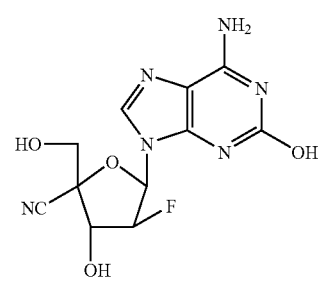
41
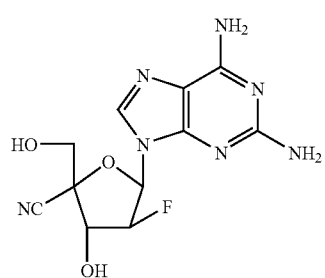
42
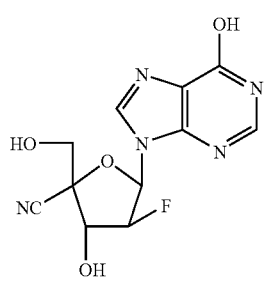
43
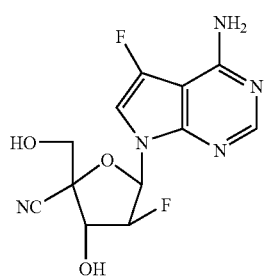
44
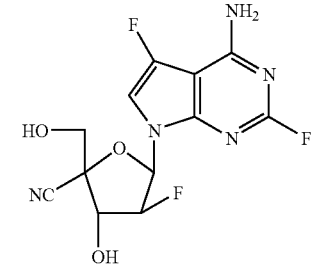

11

-continued

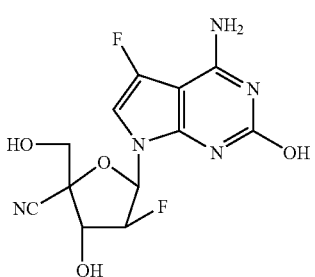

45

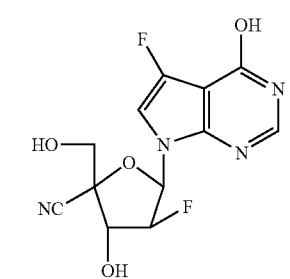

46

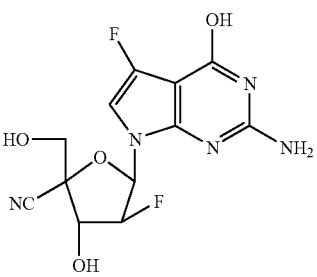

47

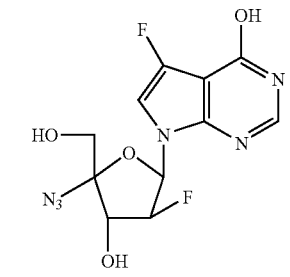

48

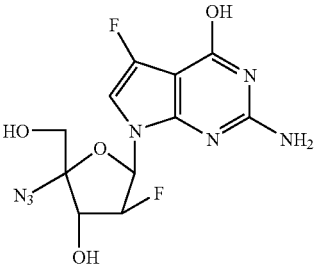

49

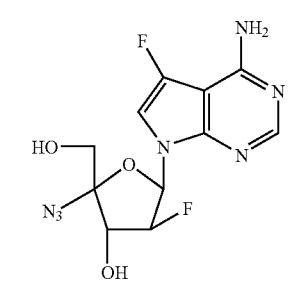

50

12

-continued

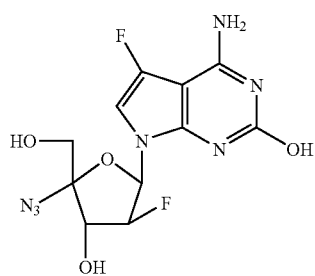

51

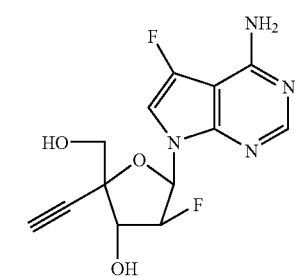

52

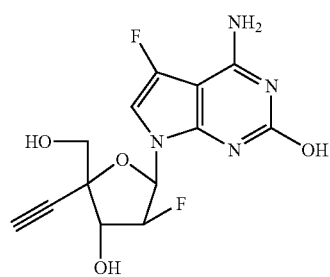

53

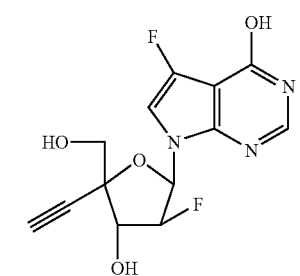

54

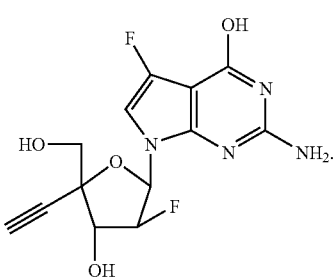

55

The present invention also relates to the uses of 2'-fluoro-4'-substituted nucleoside analogues in the preparation of medicine such as anti-viral drugs for HBV or HCV or HIV, wherein said anti-viral drugs for HBV are anti-hepatitis B virus drugs; said anti-viral drugs for HIV are anti-AIDS drugs; and said anti-viral drugs for HCV are anti-hepatitis C drugs. The present invention also relates to the preparation reaction of 2'-fluoro-4'-substituted nucleoside analogues. Where R=N₃, the reaction path is as follows:

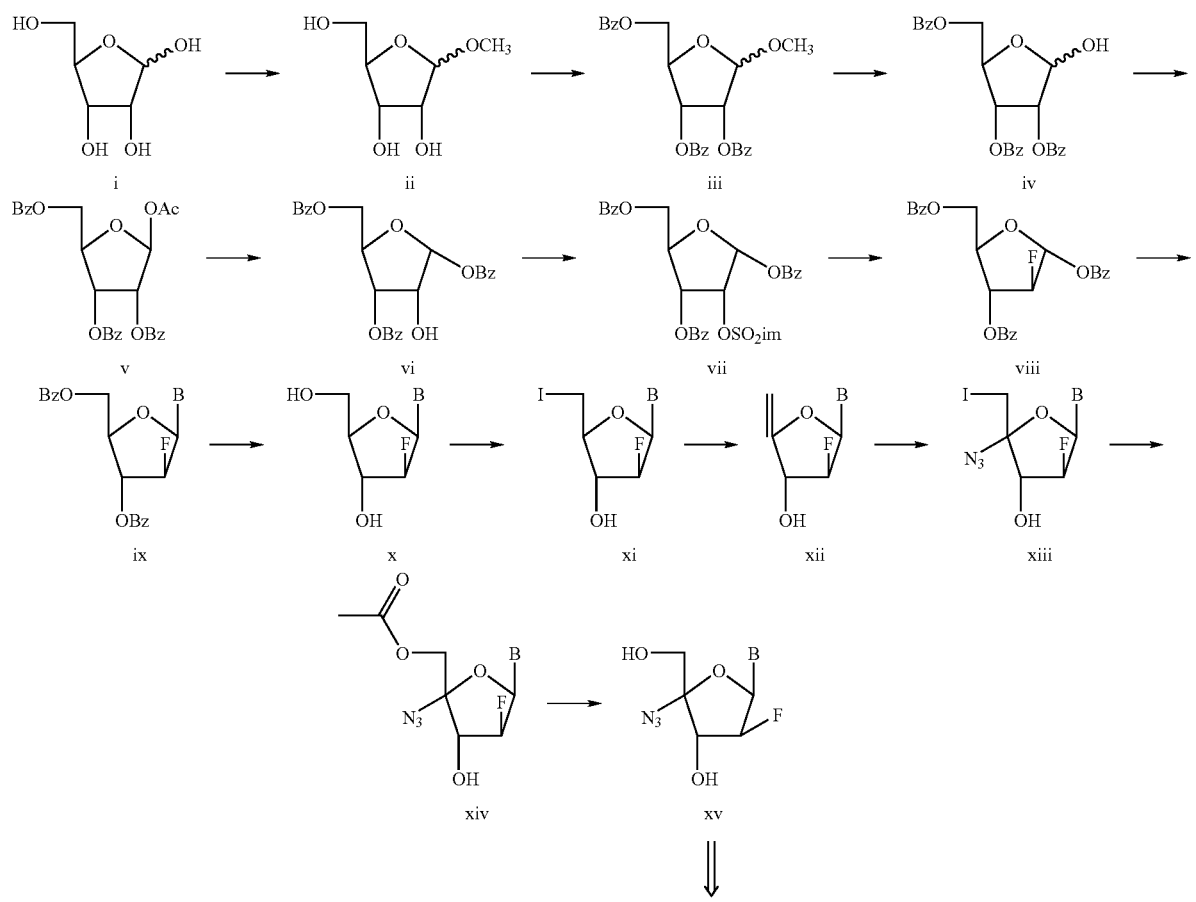

R' = H, F
X = F, OH, NH₂
Y = H, CH₃, F, OH, NH₂

The synthesis of compound ii: The compound i (D-ribose or L-ribose) is dissolved in HCl/MeOH. The solution is stirred in a water bath under hermetization and warm preservation. Pyridine is added into the solution to terminate the reaction, and then the solution is drawn off under a reduced pressure, so as to obtain light yellow syrup-like compound ii.

The synthesis of compound iii: The compound ii is dissolved in dry pyridine, and the solution is slowly added dropwise with benzoyl chloride in an ice-salt bath, and then stirred for reaction at a room temperature. After the reaction is completed, the reaction solution is poured into ice water, and extracted with chloroform. The organic layer is washed sequentially with ice water, pre-cooled sulfuric acid and saturated sodium bicarbonate until the water layer shows weak alkaline, then washed with ice water until the water layer shows neutral. The solution is dried over anhydrous sodium sulfate, and then drawn off under a reduced pressure, so as to obtain light yellow syrup-like compound iii.

The synthesis of compound iv: Benzoyl compound iii is dissolved in chloroform, red phosphorus is added, bromine is slowly added dropwise while stirring the solution in an ice-water bath. It is stirred for about 30 minutes. Then, the solution is slowly added dropwise with ice water and stirred at a room temperature. Broken ice is added into the solution and the solution is stirred until the ice is melted, and then the reaction solution is poured into ice water and extracted with chloroform. The organic layer is washed with saturated sodium bicarbonate until the water layer shows weak alkaline, and then washed with ice water until the water layer shows neutral. The solution is dried over anhydrous sodium sulfate, and then drawn off under a reduced pressure, so as to obtain dark yellow syrup. Finally the syrup is separated by silica gel column, so as to obtain white dry syrup compound iv.

The synthesis of compound v: The compound iv is dissolved in dry pyridine, the solution is slowly added dropwise with acetic anhydride in an ice water bath, and then stirred for about 30 minutes. Then, the ice water bath is removed, and the solution is stirred at a room temperature for about 7 hours, and then is heated up to 40° C. This temperature is kept for about 1 hour. Broken ice is added into the solution, and the solution is stirred until the broken ice is melted. Then, the reaction solution is poured into ice water and extracted with chloroform. The organic layer is washed sequentially with ice water, pre-cooled sulfuric acid and saturated sodium bicarbonate until the water layer shows weak alkaline, then washed with ice water until the water layer shows neutral, dried over anhydrous sodium sulfate, and then drawn off under a reduced pressure, so as to obtain light yellow syrup-like compound v.

The synthesis of compound vi: The compound v is dissolved in dry dichloromethane and the dry HCl gas is slowly introduced into an ice-water bath. The solution is washed with ice water so that an organic layer is separated. The organic layer is washed with saturated sodium bicarbonate until the water layer shows weak alkaline, and then washed with ice water until the water layer shows neutral, dried over anhydrous sodium sulfate, and drawn off under a reduced pressure to obtain light yellow syrup. The syrup is recrystallized to obtain white solid compound vi.

The synthesis of compound vii: The compound vi is dissolved in dry dichloromethane and dry DMF, and $SO_2Cl_2$ is slowly added into the solution while stirring the solution at about −15° C. The solution is stirred at −15° C. for about 30 minutes, and naturally warmed up to a room temperature for reaction. Then, imidazole is added into the solution for three times at 0° C., and the mixed solution is stirred at a room temperature. After completion of the reaction, the reaction solution is diluted by adding $CH_2Cl_2$ and then is washed with ice water. The water layer is extracted with $CH_2Cl_2$. The organic layers are combined and then dried over anhydrous sodium sulfate, and drawn off under a reduced pressure to obtain light yellow syrup. The syrup is separated and purified by silica gel column, so as to obtain white solid compound vii.

The synthesis of compound viii: The compound vii is dissolved in ethyl acetate, and $Et_3N.3HF$ is added while stirring the solution. The solution is heated up to about 60° C. and stirred for about 3 h, and then heated up to 70° C. and stirred for about 1.5 h. It is added with ice-salt water to terminate the reaction, and then extracted with dichloromethane. Then the organic layers are combined and then washed sequentially with saline, water and saturated sodium bicarbonate, dried over anhydrous sodium sulfate, and drawn off under a reduced pressure to obtain dark yellow syrup. The syrup is purified to obtain light yellow syrup. Finally the crude product is crystallized to obtain white crystalline compound viii.

The synthesis of compound ix: The compound viii is dissolved in anhydrous dichloromethane and a mixed solution of HBr—AcOH is added. The solution is stirred for reaction at a room temperature. After completion of the reaction, the mixture is evaporated to dryness, and the residue is dissolved by dichloromethane. The dichloromethane solution is washed with sodium bicarbonate solution, and dichloromethane is removed through evaporation to obtain a syrup-like product. Meanwhile, the protected cytosine and $(NH_4)_2SO_4$ are refluxed under nitrogen protection in HMDS. After the completion of reaction, the solvent is removed through evaporation under reduced pressure to obtain the silylated cytosine. The syrup obtained in the above reaction is dissolved in dichloroethane, and then added into the silylated cytosine. Then the mixture is refluxed under $N_2$ protection, and the reaction is terminated by ice. Then the solution is extracted by dichloromethane, and the dichloromethane layer is washed sequentially with saturated sodium bicarbonate and saline, and dried over anhydrous sodium sulfate. After drying the solvent is removed through evaporation to get white solid, the white solid is separated and purified by column chromatography to obtain the compound ix.

The synthesis of compound x: The compound ix is dissolved in saturated $NH_3$—$CH_3OH$ and is stirred for reaction at room temperature. After completion of the reaction, the solvent is evaporated to dryness, and the obtained residue is purified by column chromatography to obtain the compound x.

The synthesis of compound xi: The compound x, imidazole and triphenylphosphine are dissolved in tetrahydrofuran, and the solution is slowly added dropwise with iodiferous tetrahydrofuran. The solution is stirred for reaction at a room temperature. After completion of the reaction, the solvent is removed through evaporation, and the residue is added with ethyl acetate and filtered. The ethyl acetate is removed through evaporation and the residue is separated by column chromatography to obtain the compound xi.

The synthesis of compound xii: The compound xi is dissolved in tetrahydrofuran, and then the solution is added with DBU, being stirred for reaction at about 60° C. After completion of the reaction, the solvent is evaporated to dryness, and the residue is separated by column chromatography to obtain the compound xii.

The synthesis of compound xiii: The DMF solution dissolved with ICl is added in the DMF solution dissolved with $NaN_3$ at about 0° C. The solution is stirred at the freezing point for about 10 minutes and is slowly added dropwise with DMF solution dissolved with the compound xii to continue the reaction. After completion of the reaction, the mixed solution is added with sodium sulfite until the color of iodine disappears completely. The solvent is removed through evaporation under a reduced pressure, and the residue is separated and purified by column chromatography, so as to obtain the compound xiii.

The synthesis of compound xiv: The compound xiii is dissolved in DMF, silver acetate is added while stirring, and the reaction is carried out at a room temperature. After completion of the reaction, the solution is filtered. The solvent is removed under a reduced pressure and the residue is purified by column chromatography, so as to obtain the compound xiv.

The synthesis of compound xv: The compound xiv is dissolved in the solution of methanol-triethylamine, and the solution is stirred for reaction at a room temperature. After completion of the reaction, the solvent is removed through evaporation and the residue is purified by column chromatography, so as to obtain the compound xv.

The present invention also relates to the preparation reaction for 2'-fluoro-4'-substituted nucleoside analogues. Where R=$CH_3$, CN, C≡CH, the reaction path is as follows:

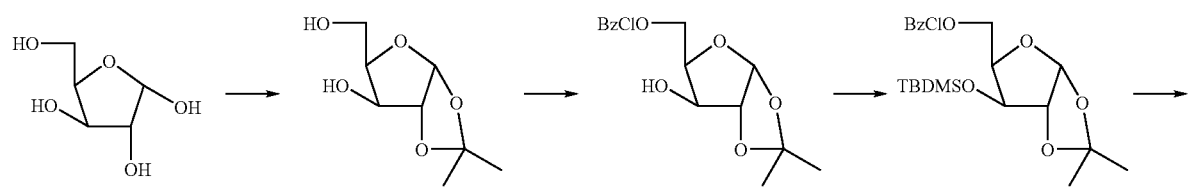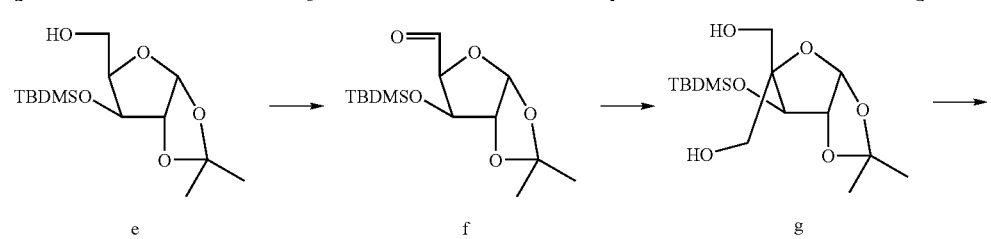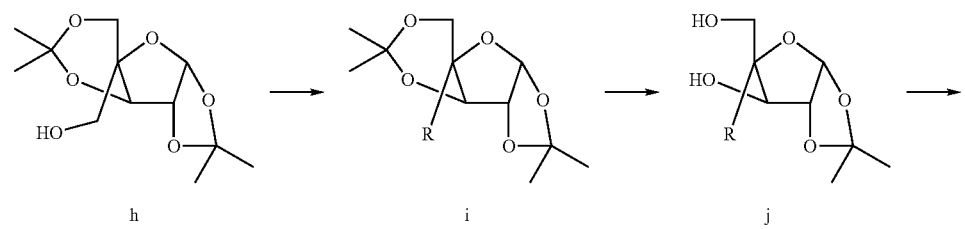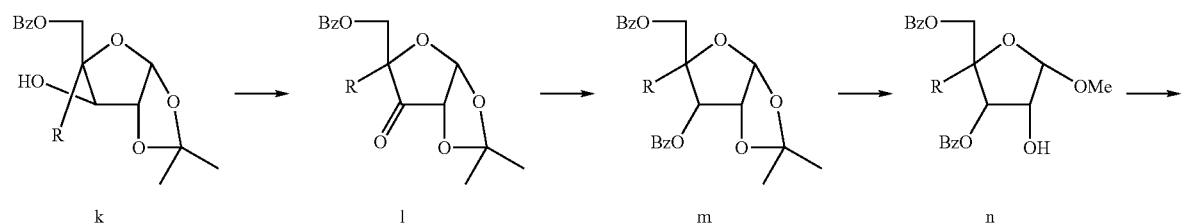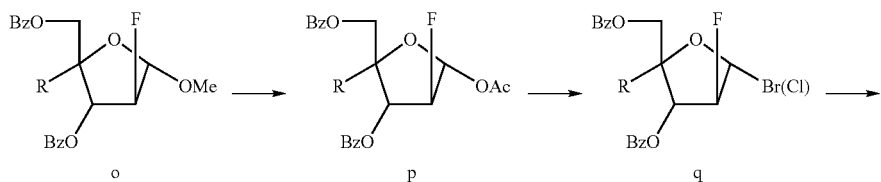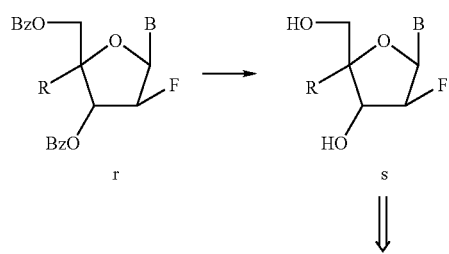

-continued

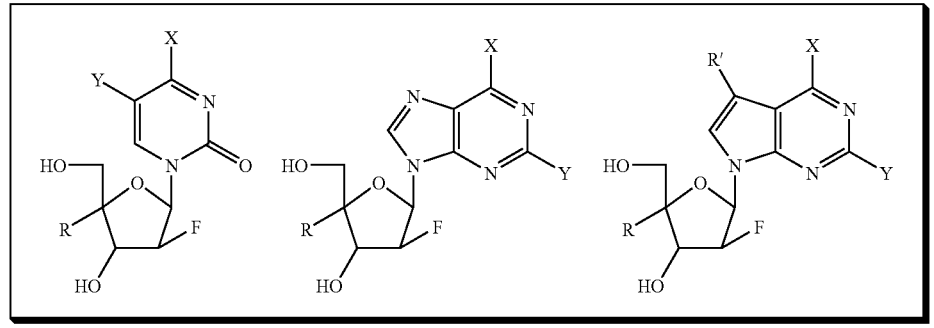

TBDMS = t-butyldimethylsilyl
R = CH₃, CN, —C≡CH
R' = H, F
X = F, OH, NH₂
Y = H, CH₃, F, OH, NH₂

The synthesis of compound b: Compound a is added in acetone, the concentrated sulfuric acid is slowly added while stirring the solution at a room temperature, and the solution is stirred for reaction at a room temperature. After the reaction is detected by TLC as complete, the solution is added with the concentrated ammonia to adjust pH, filtered, and evaporated under a reduced pressure to remove most of the acetone. Then 0.4% dilute hydrochloric acid is added while stirring, and the reaction is completed under the acetone reflux condition until compound a has been completely hydrolyzed into compound b. Then the reaction solution is neutralized by solid NaHCO₃, then filtered, and evaporated to remove the solvent under a reduced pressure. The residue is dissolved by dichloromethane, dried over anhydrous Na₂SO₄ for overnight and then filtered, and then evaporated to remove the solvent, so as to obtain the yellow viscous oily compound b.

The synthesis of compound c: The compound b and triethylamine are dissolved in dichloromethane. The solution is slowly added dropwise with parachlorobenzoyl chloride in an ice salt bath, and mechanically stirred for reaction at a temperature below 0° C. After completion of the reaction, the solution is added with a saturated NaHCO₃ solution. The dichloromethane layer is washed with water and saturated salt water, dried over anhydrous MgSO₄, filtered, and then evaporated under a reduced pressure to remove the solvent. The residue is recrystallized to obtain the white crystalline compound c.

The synthesis of compound d: The compound c is dissolved in anhydrous dichloromethane. The solution is added with imidazole and tert-butyl-2-methyl chloride silicon (TBDMSCl) under nitrogen protection for the reaction at a room temperature. After completion of the reaction, the reaction is neutralized by hydrochloric acid, and two layers are obtained. The organic layer is washed with water and saturated salt water respectively, dried over anhydrous Na₂SO₄, and then evaporated to remove the solvent. The residue is separated and purified by column chromatography, so as to obtain the compound d.

The synthesis of compound e: The compound d is dissolved in the mixed solution of sodium methoxide and methanol for reaction at a room temperature. After completion of the reaction, the solution is neutralized by dilute acetic acid, filtered, washed with methanol and then evaporated under a reduced pressure to remove the solvent. Finally the residue is separated and purified by column chromatography, so as to obtain the compound e.

The synthesis of the compound f: DMSO is added dropwise into the dichloromethane solution of oxalyl chloride at about −60° C. The solution is stirred at the same temperature for about 15 minutes, and then added dropwise with the dichloromethane solution of the compound e. After the solution is stirred for reaction at about −65° C. for about 30 minutes, triethylamine is added, and the solution is stirred for reaction at a room temperature. After completion of the reaction, water is added into the reaction solution so that the organic layer is separated, and the organic layer is dried over anhydrous magnesium sulfate. The solvent is removed through evaporation and the residue is separated and purified by column chromatography, so as to obtain the compound f.

The synthesis of compound g: Sodium hydroxide and water are added in the reaction bottle. The solution is stirred evenly and then added with a formaldehyde solution, 95% ethanol, and then the compound f. The solution is stirred for reaction at about 35° C. After completion of the reaction, the reaction bottle is cooled with ice water while stirring until the product is completely precipitated. After the suction filtration, the solid product is washed with water to neutral, dried, dissolved in anhydrous methanol, and then sodium borohydride is added for reflux reaction. After completion of the reaction, the reaction solution is neutralized by dilute hydrochloric acid and then extracted with dichloromethane, dried over anhydrous Na₂SO₄. The solvent is removed by evaporation so that the compound g is obtained.

The synthesis of compound h: The compound g is dissolved in methanol, and the solution is added with Dowex H⁺ (washed with methanol in advance) for reaction at a room temperature. After completion of the reaction, the resin is removed from the solution through filtration and repeatedly washed with methanol. The solution is evaporated to obtain the solid substance. The obtained solid substance is dissolved in acetone, and then concentrated sulfuric acid (catalytic amount) is slowly added into the solution for reaction at a room temperature while stirring. The reaction solution is added with concentrated ammonia water to adjust pH value, and then filtered and evaporated under a reduced pressure to remove acetone, so as to obtain the compound h.

The synthesis of compound i: DMSO is added dropwise into the dichloromethane solution of oxalyl chloride at −60° C. Then, the solution is stirred for about 15 minutes and then is added dropwise with the dichloromethane solution of the compound h. After the reaction is carried out for 30 minutes at −60° C., triethylamine is added in the solution to continue the reaction at a room temperature for 30 minutes. Then, water is added to terminate the reaction, and the organic layer is separated and dried over anhydrous $Na_2SO_4$. The solvent is removed through evaporation and the residue is separated and purified by column chromatography to obtain the solid product. $ClCH_2P(C_6H_5)_3Cl$ is added into anhydrous tetrahydrofuran. The solution is cooled to about −78° C., added with n-BuLi hexane solution, stirred for reaction for about 1 h, then added with the dry tetrahydrofuran solution of the solid product. The temperature of the solution is gradually increased to about 0° C. to continue the reaction. After completion of the reaction, saturated $NH_4Cl$ solution is carefully added dropwise in the solution, and the solution is subsequently extracted with ethyl acetate. The organic layer is washed with saline twice, dried over anhydrous $MgSO_4$, and evaporated to remove the solvent. The residue obtained is dissolved into anhydrous tetrahydrofuran, cooled to about −78° C., and slowly added dropwise with n-BuLi hexane solution. After the solution is stirred for about 2 hours, the reaction is carefully terminated by using saturated $NH_4Cl$. The organic layer is washed with saturated salt water, dried over anhydrous MgSO4, and evaporated under a reduced pressure to remove the solvent. Finally the residue is separated and purified by rapid silica gel column, so as to obtain the compound i.

The synthesis of compound j: The compound i is added in the diluted hydrochloric acid solution, the solution is stirred at a room temperature for reaction. After completion of the reaction, the solution is neutralized by solid $NaHCO_3$, and then filtered. The filtrate is evaporated under a reduced pressure to remove the solvent, and the residue is dissolved by dichloromethane and dried over anhydrous $Na_2SO_4$, and then filtered and evaporated to remove the solvent, so as to obtain the compound j.

The synthesis of compound k: The compound j is dissolved in pyridine, and the solution is added dropwise with BzCl for reaction at a room temperature. After completion of the reaction, the solvent is evaporated to dryness, and the residue is purified to obtain the compound k.

The synthesis of compound l: The compound k and 2,2,6,6-tetramethyl piperidine-N-oxide are dissolved in dichloromethane, the solution is cooled to about 0° C. and added with the mixed solution of sodium hypochlorite solution, $NaHCO_3$ and water for reaction at about 0° C. for about 30 minutes. Isopropanol is added into the reaction solution and stirred at a room temperature. The separated dichloromethane layer is washed with water twice, dried over anhydrous $MgSO_4$, filtered, and evaporated to remove the solvent. The obtained residue is recrystallized to obtain the compound l.

The synthesis of compound m: The compound l is dissolved in the mixed solution of absolute ethanol and ethyl acetate. The solution is cooled to about 0° C., and then added with sodium borohydride in batches, being stirred for reaction. After completion of the reaction, the reaction solution is neutralized with a dilute acetic acid solution, filtered, and the filtrate is evaporated. The residue is dissolved in dichloromethane and then washed with water. The dichloromethane layer is dried over anhydrous $MgSO_4$, filtered, and evaporated to remove the dichloromethane under a reduced pressure. The residue is recrystallized by the mixed solvent of dichloromethane and petroleum ether to obtain solid substance. Then the solid product is dissolved in pyridine. BzCl is added dropwise at about 0° C., and after that the reaction goes on at a room temperature. After completion of the reaction, the solvent is removed through evaporation and the residue is extracted with ethyl acetate, washed with saturated $NaHCO_3$ solution, dried over anhydrous $Na_2SO_4$, filtered, evaporated to remove the solvent, so that the compound m is obtained.

The synthesis of compound n: The compound m is dissolved in methanol, and then the solution is added with the mixed solution of concentrated hydrochloric acid/dioxane for reaction at a room temperature. After completion of the reaction, the reaction solution is neutralized with $NaHCO_3$, and filtered. The solvent is removed from the filtrate by vacuum distillation, and the residue is dissolved in an appropriate amount of dichloromethane and dried over anhydrous $Na_2SO_4$ for overnight and then filtered, evaporated to dryness, and finally separated and purified by column chromatography to obtain the compound n.

The synthesis of compound o: The compound n is dissolved in dichloromethane, and the solution is added with DAST under a room temperature and stirred for reaction. After completion of the reaction, the solution is poured into saturated $NaHCO_3$ solution and the organic layer is separated. The organic layer is washed with saturated $NaHCO_3$ solution, dried over anhydrous $Na_2SO_4$, and separated and purified by column chromatography to obtain the compound o.

The synthesis of compound p: The compound o is added in formic acid solution, and the solution is stirred at a room temperature for reaction. After completion of the reaction, the solution is evaporated under a reduced pressure to remove the solvent. The residue and toluene are evaporated together to obtain the solid product. The obtained solid product is dissolved in the solution of dry pyridine and acetic anhydride for reaction at a room temperature. After the reaction is completed, the reaction solution is concentrated and then evaporated together with toluene, so as to obtain the compound p.

The synthesis of compound q: The compound p is dissolved in anhydrous dichloromethane and cooled to about 0° C. The HCl gas is slowly introduced into the solution to a saturation level and the solvent is removed by vacuum evaporation at a room temperature. The residue is dried in vacuum to obtain the compound q.

The synthesis of compound r: With the existence of $(NH_4)_2SO_4$, 2,6-diamino-purine and Hexamethyldisilazane (HMDS) are heated and refluxed to be a transparent solution. The solvent is removed under vacuum to obtain a white solid product, and the solid product is subsequently dissolved in 1,2-dichloroethane. Then, 1,2-dichloroethane solution of compound q and molecular sieve are added, the solution is stirred for reaction under nitrogen protection at a room temperature. After the reaction is detected by TLC as complete, the reaction solution is added with dichloromethane and filtered by diatomite. The filtrate is washed with saturated $Na_2SO_4$ and saline respectively. The organic layer is dried over anhydrous $Na_2SO_4$ overnight and the solvent is removed through evaporation to obtain the residue. The residue is separated under a reduced pressure through silica gel column, so as to obtain the compound r.

The synthesis of compound s: The compounds r is dissolved in saturated $NH_3$—$CH_3OH$ solution, and the solution is stirred for reaction at a room temperature. After completion of the reaction, the solvent is removed through evaporation and the residue is separated and purified by column chromatography, so as to obtain the compound s.

The beneficial effects of the present invention lie in that, by means of chemical modifications made to the glycosyl and base, D- and L-nucleoside analogue would contain special structures such as fluoric group, alkynyl, azide and cyano etc. and thus can overcome the deficiencies of the present D- and L-nucleoside analogues, including more toxic side effect and less activity. Furthermore, the synthesis method is simple and feasible with high yield ratio, having a good value when it is used in the preparation of anti-HBV or anti-HCV or anti-HIV drugs.

SPECIFIC EMBODIMENTS

The present invention is further described hereinafter according to the synthetic route of the compound expressed in the general formula I in combination with the preferred embodiments. However, these preferred embodiments provided are not to limit the scope of the present invention.

Example 1

The Synthesis of the Compound 15 Wherein the Base is Cytosine

The synthesis of compound ii: The compound i (D-ribose or L-ribose) (8.66 mmol) was dissolved in 31.2 ml HCl/MeOH (0.2 mmol/L), and the solution was stirred in a water bath at 27° C. for 3 hours under hermetization and warm preservation. The solution was added with 7.8 ml pyridine to terminate the reaction, and then drawn off under a reduced pressure, so as to obtain the light yellow syrup-like compound ii (96%);

The synthesis of compound iii: The compound ii (7.92 mmol) was dissolved in 21 ml dry pyridine, and 5.2 ml benzoyl chloride (0.0447 mol) was slowly added dropwise in the solution in an ice-salt bath. The solution was stirred at a room temperature for 17 hours. The reaction solution was poured into 39 ml ice water, and extracted with chloroform. The organic layer was washed sequentially with ice water, pre-cooled sulfuric acid (3 mol/L) and saturated sodium bicarbonate solution until the water layer shows weak alkaline, and then washed with ice water until the water layer shows neutral, dried over anhydrous sodium sulfate for more than 4 hours, and drawn off under a reduced pressure, so as to obtain the light yellow syrup-like compound iii (80.0%). $^1$H NMR (CDCl$_3$) δ ppm: 7.28~8.10 (m, 15H, OBz), 5.87 (m, 1H, H-3), 5.68 (d, 1H, H-2), 5.16 (s, 1H, H-1), 4.72 m, 2H, H-5), 4.52 (q, 1H, H-4), 3.42 (s, 3H, OCH$_3$).

The synthesis of compound iv: Benzoyl compound iii (0.0027 mol) was dissolved in chloroform (13 mol), red phosphorus (390 mg, 0.0126 mol) was added, and bromine (1.3 ml, 0.025 mmol) was slowly added dropwise while stirring the solution in an ice-water bath. After stirring it for 30 minutes, 1.3 ml ice water was slowly added dropwise and the solution was stirred at a room temperature for 4 hours. 7 g broken ice was added and stirred to melt the broken ice. Then the reaction solution was poured into 14 ml ice water and extracted with chloroform. The organic layer was washed with saturated sodium bicarbonate until the water layer shows weak alkaline, and then washed with ice water until the water layer shows neutral, and then dried over anhydrous sodium sulfate for over 4 hours, and then drawn off under a reduced pressure to obtain the dark yellow syrup. Finally the syrup was separated by silica gel column (gradient elution, petroleum ether: acetone), so as to obtain the white dry syrup compound iv (64.2%). $^1$H NMR (CDCl$_3$) δ ppm: 7.32~8.10 (m, 15H, OBz), 5.90 (m, 1H, H-3), 5.70 (d, 1H, H-2), 5.63 (s, 1H, H-1), 4.55~4.79 (m, 3H, H-5, H-4).

The synthesis of compound v: The compound iv (2.73 mmol) was dissolved in 5 ml dry pyridine, and the solution was slowly added dropwise with acetic anhydride (0.0276 mol) in an ice water bath, then stirred for 30 minutes. Then, the ice water bath was removed, and the solution was stirred at a room temperature for 7 hours, and then heated up to 40° C. This temperature was kept for an hour. The solution was added with 6.5 g broken ice and then stirred until the broken ice was melted. The reaction solution was poured into 13 ml ice water and extracted with chloroform. The organic layer was washed sequentially with ice water, pre-cooled sulfuric acid (3 mol/L) and saturated sodium bicarbonate until the water layer shows weak alkaline, then washed with ice water until the water layer shows neutral, dried over anhydrous sodium sulfate for more than 4 hours, and then drawn off under a reduced pressure, so as to obtain the light yellow syrup-like compound v (92.1%). $^1$H NMR (CDCl$_3$) δ ppm: 7.30~8.10 (m, 15H, OBz), 6.43 (s, 1H, H-1), 5.90 (m, 1H, H-3), 5.80 (d, 1H, H-2), 4.50~4.80 (m, 2H, H-5), 2.00 (s, 3H, CH$_3$COO—).

The synthesis of compound vi: The compound v (2.57 mmol) was dissolved in 26 ml dry dichloromethane and dry HCl gas was slowly introduced into an ice-water bath for 2.5 hours. The solution was washed with 19.5 ml ice water and the organic layer was separated. The organic layer was washed with saturated sodium bicarbonate until the water layer shows weak alkaline, and then washed with ice water until the water layer shows neutral, dried over anhydrous sodium sulfate for more than 4 hours, and then drawn off under a reduced pressure to obtain light yellow syrup. The syrup was recrystallized using the mixed solvent of hexane and dichloromethane, so as to obtain the white solid compound vi (65.1%). $^1$H NMR (CDCl$_3$) δ ppm: 7.36~8.14 (m, 15H, OBz), 6.68 (d, J=4.4 Hz, 1H, H-1), 5.59 (dd, 1H, H-3), 4.64~4.80 (m, 4H, H-2, H-4 and H-5). M.p. 139-140° C.

The synthesis of compound vii: The compound vi (2.81 mmol) was dissolved in 13 ml dry dichloromethane and 3.5 ml dry DMF, and SO$_2$Cl$_2$ (0.0079 mmol) was slowly added while stirring the solution at −15° C. After it was stirred at −15° C. for about 30 minutes, the solution was naturally warmed up to a room temperature, reacting for 3 hours. Then the solution was added with imidazole (0.0407 mmol) for three times at 0° C. The mixed solution was stirred at a room temperature for 15 hours. The reaction solution was diluted with CH$_2$Cl$_2$ (26 ml) added, and washed with ice water (35 ml). The water layer was extracted with CH$_2$Cl$_2$. Then the organic layers were combined and then dried over anhydrous sodium sulfate for over 4 hours, and then drawn off under a reduced pressure to obtain light yellow syrup. The syrup was separated and purified by silica gel column (gradient elution, petroleum ether: acetone) to obtain the white solid compound vii (76.0%). $^1$H NMR (CDCl$_3$) δ ppm: 7.00~8.10 (m, 15H, OBz), 6.71 (d, J=4.4 Hz, 1H, H-1), 5.59 (dd, 1H, H-3), 5.25 (dd, 1H, H-2), 4.56~4.81 (m, 3H, H-4, H-5). M.p. 128~129° C.

The synthesis of compound viii: The compound vii (2.2 mmol) was dissolved in ethyl acetate (54 ml), and Et$_3$N.3HF (2.08 ml, 0.013 mmol) was added while stirring the solution. The solution was heated up to 60° C., stirred for 3 h, and then heated to 70° C. and stirred for 1.5 h. The solution was added with ice-salt (10 ml) to terminate the reaction, and extracted with dichloromethane. The organic layers were combined and then washed sequentially with saline, water and saturated sodium bicarbonate, and dried over anhydrous sodium sulfate for over 4 hours. The solvent was drawn off under a reduced pressure to obtain dark yellow syrup. The syrup was purified (dichloromethane elution) by means of a silica gel funnel (5 cm×5 cm) to yield light yellow syrup (86.8%). Finally the crude product was crystallized in 95% ethanol solution to obtain the white compound viii crystalline (66.4%). $^1$H NMR (CDCl$_3$) δ ppm: 7.31~8.10 (m, 15H, OBz), 6.71 (d, J=9.0 Hz, 1H, H-1), 5.68 (dd, J=19.44 Hz, 1H, H-3), 5.32 (d, J=48.2 Hz, 1H, H-2), 4.65~4.77 (m, 3H, H-4, H-5). M.p. 80~82° C.

The synthesis of compound ix: The compound viii (6.0 mmol) was dissolved in anhydrous dichloromethane (20 ml), and a mixed solution of HBr—AcOH (45%, V/V, 4.6 ml, 25 mmol) was added in the solution. The solution was stirred for reaction at a room temperature for 20 hours. The mixture was evaporated to dryness. The residue was dissolved by dichloromethane (50 ml). The dichloromethane solution was washed with sodium bicarbonate solution (3×30 ml), and dichloromethane was removed through evaporation to obtain a syrup-like product. Meanwhile, the protected cytosine (15 mmol) and $(NH_4)_2SO_4$ (0.1 g) were refluxed for 17 hours under nitrogen protection in HMDS (30 ml). After completion of reaction, the solvent was removed through evaporation under a reduced pressure to obtain silylated cytosine. The syrup obtained in the above reaction was dissolved in dichloroethane (25 ml), and added into the silylated cytosine. Then the mixture was refluxed for 15 hours under $N_2$ protection and the reaction was terminated by ice. Then, the solution was extracted with dichloromethane (3×45 ml) and the dichloromethane layer was washed sequentially with saturated sodium bicarbonate and saline, and dried over anhydrous sodium sulfate. After drying, the solvent was removed through evaporation to yield white solid, and the solid was separated and purified by column chromatography (1% MeOH—$CHCl_3$) to obtain the compound ix (71%). $^1H$ NMR ($CDCl_3$) δ ppm: 8.07 (d, J=9.86 Hz, 1H), 7.45 (d, J=9.82 Hz, 1H), 7.26-8.10 (m, 10H, OBz), 6.03 (d, J=9.0 Hz, 1H, H-1), 5.64 (dd, J=19.44 Hz, 1H, H-3), 5.26 (d, J=48.2 Hz, 1H, H-2), 4.65~4.77 (m, 3H, H-4, H-5).

The synthesis of compound x: The compound ix (3.60 mmol) was dissolved in saturated $NH_3$—$CH_3OH$ (30 ml), and the solution was stirred for reaction at a room temperature for 15 hours. After completion of the reaction, the solvent was evaporated to dryness to obtain the residue, and the residue was purified by column chromatography (15:1 $CHCl_3$-MeOH) to obtain the compound x (80%). $^1H$ NMR ($CDCl_3$) δ ppm: 8.10 (d, J=9.86 Hz, 1H), 7.40 (d, J=9.82 Hz, 1H), 6.03 (d, J=9.0 Hz, 1H, H-1), 5.64 (dd, J=19.44 Hz, 1H, H-3), 5.26 (d, J=48.2 Hz, 1H, H-2), 4.50 (m, 1H, H-4), 3.70~3.77 (m, 2H, H-5).

The synthesis of compound xi: The compound x (9.46 mmol), imidazole (18.93 mmol) and triphenylphosphine (14.19 mmol) were dissolved in tetrahydrofuran (50 ml). The solution was slowly added dropwise with 15 ml iodiferous tetrahydrofuran (14.18 mmol). The solution was stirred for reaction at a room temperature for 3 hours. After completion of the reaction, the solvent was removed through evaporation to obtain the residue, and the residue was added with ethyl acetate (100 ml) and filtered. The ethyl acetate was removed through evaporation and the residue was separated by column chromatography to obtain the compound xi (83.9%). $^1H$ NMR ($CDCl_3$) δ ppm: 8.06 (d, J=9.86 Hz, 1H), 7.43 (d, J=9.82 Hz, 1H), 6.01 (d, J=9.0 Hz, 1H, H-1), 5.66 (dd, J=19.44 Hz, 1H, H-3), 5.22 (d, J=48.2 Hz, 1H, H-2), 4.57 (m, 1H, H-4), 3.58~3.69 (m, 2H, H-5).

The synthesis of compound xii: The compound xi (5.88 mmol) was dissolved in tetrahydrofuran (50 ml), and the solution was added with DBU (6.44 mmol) and then stirred at 60° C. for 3 hours. The solvent was evaporated to dryness, and the residue was separated by column chromatography to obtain the compound xii (75.1%) which is directly used in the next reaction.

The synthesis of compound xiii: The 15 ml DMF solution dissolved with ICl (13.9 mmol) was added in the DMF (15 ml) solution dissolved with $NaN_3$ (9.75 mmol) at 0° C. The solution was stirred at 0° C. for 10 minutes and was slowly added dropwise with DMF (20 ml) dissolved with the compound xii (6.8 mmol) to continue the reaction at 0° C. for an hour. After completion of the reaction, the mixed solution was added with sodium sulfite until the color of iodine disappears completely. The solvent was removed through evaporation under a reduced pressure, and the residue was separated and purified by column chromatography to obtain the compound xii (77.6%) which is directly applied in the next reaction.

The synthesis of compound xiv: The compound xiii (5 mmol) was dissolved in DMF (15 ml), and the solution was added with silver acetate (6 mmol) and stirred. After the reaction was carried out at a room temperature for 8 hours, the solution was filtered and the solvent was removed under a reduced pressure (at a temperature below 50° C.). The residue was purified by column chromatography to obtain the compound xiv (71.3%). $^1H$ NMR (DMSO-$d_6$, 300 MHz) δ: 8.12 (d, 1H), 7.40 (d, 1H), 7.26 (br, 2H), 6.12 (dd, 1H), 5.87 (d, 1H), 5.09 (t, 1H), 4.90 (dt, 1H), 4.18 (dt, 1H), 3.74-3.87 (m, 2H), 2.12 (s, 3H, $CH_3$).

The synthesis of compound xv: The compound xiv (5 mmol) was dissolved in 5% methanol-triethylamine (100 ml), and the solution was stirred at a room temperature for 12 hours. After completion of the reaction, the solvent was removed through evaporation and the residue was purified by column chromatography to obtain the compound xv (89.0%). ESI-MS: 287[M+H]. $^1H$ NMR (DMSO-$d_6$, 300 MHz) δ: 8.14 (d, 1H), 7.32 (d, 1H), 7.21 (br, 2H), 6.08 (dd, 1H), 5.82 (d, 1H), 5.11 (t, 1H), 4.92 (dt, 1H), 4.16 (dt, 1H), 3.62-3.69 (m, 2H).

Example 2

The Synthesis of the Compounds 25, Wherein the 4'-Substitued Group is Alkynes and the Base is 1,6-Diamino-Purine The synthesis of compound b: Compound a (60 g) was added in acetone (2 L) and the concentrated sulfuric acid (40 ml) was slowly added while stirring. The solution was stirred for reaction at a room temperature for 40 minutes. After the reaction was detected by TLC as complete, the solution was added with the concentrated ammonia to adjust pH=7~8, filtered, and evaporated under a reduced pressure to remove most of the acetone. The remaining acetone and water were about 150 ml. Then the solution was added with 0.4% dilute hydrochloric acid (150 ml) while being stirred, and the reaction was completed under the acetone reflux condition for 20 minutes until the compound a has been completely hydrolyzed into the compound b. After completion of the reaction, the reaction solution was neutralized to pH=7~8 by solid $NaHCO_3$, filtered, and evaporated to remove the solvent under a reduced pressure. The residue was dissolved with dichloromethane (200 ml), dried over anhydrous $Na_2SO_4$ overnight and then filtered. Finally the solvent was removed through evaporation to obtain the yellow viscous oily b (73 g, 95%), ESI-MS: 191[M+H].

The synthesis of compound c: The compound b (154 g, 0.81 mol) and triethylamine (339 ml, 2.43 mol) were dissolved in dichloromethane (1.50 L). The solution was cooled to 0° C. in an ice salt bath, slowly added dropwise with parachlorobenzoyl chloride (113 ml, 0.891 mol) and mechanically stirred for reaction at a temperature below 0° C. for 4 hours. After completion of the reaction, the solution was added with a saturated $NaHCO_3$ solution (500 ml). The dichloromethane layer was washed with water and saturated salt water, dried over anhydrous $MgSO_4$, filtered, and evaporated under a reduced pressure to remove the solvent. The residue was recrystallized to obtain white crystalline compound c (196 g, yield=74.6%), ESI-MS: 330[M+H].

The synthesis of compound d: The compound c (0.114 mol) was dissolved in anhydrous dichloromethane (600 ml), and the solution was added with imidazole (15.5 g, 0.228 mol) and tert-butyl-dimethyl chloride silicon (TBDMSCl) (18.9 g, 0.125 mol) under nitrogen protection for the reaction for 3 hours at a room temperature. After completion of the reaction, 1N hydrochloric acid was added to neutralize the reaction and two reaction layers were obtained. The organic layer was washed with water and saturated salt water, dried over anhydrous $Na_2SO_4$, and evaporated to remove the solvent. The residue was separated and purified by column chromatography to obtain compound d (yield=69.2%), ESI-MS: 444[M+H].

The synthesis of compound e: The compound d (0.64 mmol) was dissolved in the mixed solution (0.2N, 15 ml) of sodium methoxide and methanol for reaction for 4 hours at a room temperature. After completion of the reaction, the solution was neutralized by dilute acetic acid, filtered, washed with methanol and evaporated under a reduced pressure to remove the solvent. Finally the residue was separated and purified by column chromatography to obtain compound e (yield=75%), ESI-MS: 305[M+H].

The synthesis of compound f: DMSO (5.5 ml, 77.5 mmol) was added dropwise into the dichloromethane (80.0 ml) solution of oxalyl chloride (3.4 ml, 38.7 mmol) at −60° C. The solution was stirred at the same temperature for 15 minutes and then added dropwise with the dichloromethane solution (100 ml) of the compound e (25.7 mmol). After the solution was stirred for reaction at −65° C. for 30 minutes, triethylamine (10.9 ml, 78.2 mmol) was added to continue the reaction for 30 minutes and the solution was stirred at a room temperature. After completion of the reaction, water was added in the reaction mixture so that the organic layer is separated. The organic layer was dried over anhydrous magnesium sulfate. Finally the solvent was removed through evaporation and the residue was separated and purified by column chromatography to obtain the compound f (yield=94.6%), ESI-MS: 303[M+H].

The synthesis of compound g: Sodium hydroxide (1.3 g) and water (11.5 ml) were added in the reaction bottle. The solution was stirred evenly and added with formaldehyde solution (30%), 7.2 ml 95% ethanol, and then the compound f (25 mmol). Then, the solution was stirred for reaction at a controlled reaction temperature of 30~35° C. for 2 hours. After completion of the reaction, the reaction bottle was cooled with ice water while stirring until the product was completely precipitated. After the suction filtration, the solid product was washed with water to neutral, dried, dissolved in anhydrous methanol, then added into sodium borohydride (0.925 g, 25 mmol) and refluxed for an hour. After completion of the reaction, the reaction solution was neutralized by dilute hydrochloric acid and extracted with dichloromethane (3×50 ml), dried over anhydrous $Na_2SO_4$. The solvent was removed by evaporation, so that the compound g was obtained (yield=90.5%, ESI-MS: 335[M+H]).

The synthesis of compound h: The compound g (9.7 mmol) was dissolved in methanol (260 ml), and the solution was added with 40 ml Dowex $H^+$ (washed with methanol in advance) for reaction at a room temperature for 4 hours. The resin was removed from the solution through filtration and repeatedly washed with methanol. The solvent was dried to obtain solid substance. The obtained solid substance was dissolved in acetone (200 ml). Then concentrated sulfuric acid (catalytic amount, 2 ml) was slowly added dropwise for reaction at a room temperature for about 0.5 hours. Then the solution was added with concentrated ammonia water to adjust pH value to 7~8, filtered, evaporated under a reduced pressure to remove most of acetone. The reaction solution was added with diluted hydrochloric acid (0.4%, 40 ml) and reacted 20 minutes under acetone refluxing. Then the reaction solution was neutralized by $NaHCO_3$ to pH=7~8, filtered, evaporated under a reduced pressure to remove the solvent. The residue was dissolved by appropriate amount of dichloromethane, dried over anhydrous $Na_2SO_4$, and evaporated to remove the solvent, so as to obtain the compound h (yield=80.2%, ESI-MS: 261[M+H])

The synthesis of compound i: DMSO (5.5 ml, 77.5 mmol) was added dropwise into the dichloromethane (80 ml) solution of oxalyl chloride (3.4 ml, 38.7 mmol) at −60° C. Then, the solution was stirred for 15 minutes and added dropwise with the dichloromethane (100 ml) solution of compound h (25.7 mmol). After the reaction was carried out for 30 minutes at −60° C., triethylamine (10.9 ml, 78.2 mmol) was added in to continue the reaction at a room temperature for 30 minutes. Then, water was added to terminate the reaction, and the organic layer was separated and dried over anhydrous $Na_2SO_4$. The solvent was removed through evaporation and the residue was separated and purified by column chromatography to obtain a solid product. $ClCH_2P$ $(C_6H_5)_3Cl$ (2.15 g, 6.19 mmol) was added into anhydrous tetrahydrofuran (50 ml). The solution was cooled to −78° C., added with n-BuLi hexane solution (1.6M, 4.0 ml), stirred for reaction for an hour, and added with the dry tetrahydrofuran solution (50 ml) of the solid product (1.51 mmol). The cooling temperature was gradually increased to 0° C. to continue the reaction for 3 hours. After completion of the reaction, a saturated $NH_4Cl$ solution (10 ml) was carefully added dropwise, and the solution was subsequently extracted with ethyl acetate (2×100 ml). The organic layer was washed with saline twice (2×75 ml), finally dried over anhydrous $MgSO_4$, and evaporated under a reduced pressure to remove the solvent. The residue produced was dissolved into anhydrous tetrahydrofuran (40 ml), cooled to −78° C., and slowly added dropwise with the hexane solution of n-BuLi (1.6M, 20 ml). After the solution was stirred for reaction for 2 hours, the reaction was terminated by carefully adding a saturated $NH_4Cl$ solution (20 ml). The organic layer was washed with saturated salt water, dried over anhydrous MgSO4, and evaporated under a reduced pressure to remove the solvent. Finally the residue was separated and purified by rapid silica gel column to obtain the compound i (yield=48.5%, ESI-MS: 255[M+H]).

The synthesis of compound j: The compound i (10 mmol) was added into the diluted hydrochloric acid solution (0.2%, 50 ml) and stirred for reaction for 6 hours at a room temperature. After completion of the reaction, the solution was neutralized by solid $NaHCO_3$ to pH=7~8 and then filtered. The filtrate was evaporated under a reduced pressure to remove the solvent and the residue was dissolved with dichloromethane and dried over anhydrous $Na_2SO_4$, and then filtered and evaporated to remove the solvent, so as to obtain the compound j (yield=99.0%, ESI-MS: 215[M+H]).

The synthesis of compound k: The compound j (5 mmol) was dissolved in pyridine (20 ml), and the solution was added dropwise with BzCl (5 mmol) for reaction at a room temperature for 6 hours. After completion of the reaction, the solvent was removed through evaporation and the residue was purified to obtain the compound k (yield=85.3%, ESI-MS: 319 [M+H]).

The synthesis of compound l: The compound k (59.3 mmol) and 2,2,6,6-tetramethyl piperidine-N-oxide (0.059 mmol) were dissolved in dichloromethane (99 ml), the solution was cooled to 0° C. and added with the mixed solution of sodium hypochlorite solution (33.6 ml, 8.5~13.5% active chlorine), $NaHCO_3$ (11.2 g) and water (190 ml) for reaction at 0° C. After 30 minutes, the reaction solution was added with isopropanol (1.95 ml) and stirred for reaction at a room temperature for 10 minutes. The dichloromethane layer separated was washed with water twice, dried over anhydrous MgSO$_4$, filtered, and then evaporated to remove the solvent. The residue obtained was recystalized to obtain the crystalline compound l (yield=87.8%, ESI-MS: 317[M+H]).

The synthesis of compound m: The compound l ((0.05 mol) was dissolved in the mixed solution of absolute ethanol (60 ml) and ethyl acetate (30 ml); the solution was cooled to 0° C., and then added with sodium borohydride (23.3 g, 612 mmol) in batches, being stirred for reaction at 0° C. for an hour. After completion of the reaction, the reaction solution was neutralized with dilute acetic acid solution to pH=7~8, filtered, and the filtrate was evaporated. The residue was dissolved in dichloromethane and washed with water. The dichloromethane layer was dried over anhydrous MgSO$_4$, filtered, and evaporated to remove the dichloromethane under a reduced pressure. The residue was recrystallized by the mixed solvent of dichloromethane and petroleum ether to produce a solid product. Then the solid product was dissolved in pyridine. BzCl (50 mmol) was added dropwise at 0° C., and after that, the reaction goes on at a room temperature for 3 hours. After completion of the reaction, the solvent was removed through evaporation and the residue was extracted with ethyl acetate, washed with saturated NaHCO$_3$ solution, dried over anhydrous Na$_2$SO$_4$, filtered, evaporated to remove the solvent, so that the compound m was obtained (yield=89.7%, ESI-MS: 423[M+H]).

The synthesis of compound n: The compound m (4 mmol) was dissolved in methanol (22 ml), and then the solution was added with the mixed solution (4.0M, 20 ml) of concentrated hydrochloric acid/dioxane for reaction at a room temperature for 10 hours. After completion of the reaction, the reaction solution was neutralized with NaHCO$_3$ to pH=7~8 and filtered. The filtrate was distilled under a reduced pressure to remove the solvent, and the residue was dissolved in an appropriate amount of dichloromethane, dried over anhydrous Na$_2$SO$_4$ for overnight, then filtered, evaporated to dryness, and finally separated and purified by column chromatography to obtain the compound n (yield=89.5%, ESI-MS: 397[M+H]).

The synthesis of compound o: The compound n (1.76 mmol) was dissolved in dichloromethane, and the solution was added with DAST (0.4 ml, 3.03 mmol) under a room temperature and stirred for 12 hours. After completion of the reaction, the solution was poured into 10 ml saturated NaHCO$_3$ solution and the organic layer was separated. The organic layer was washed with saturated NaHCO$_3$ solution, dried over anhydrous Na$_2$SO$_4$, and separated and purified by column chromatography to obtain the compound o (yield=11.5%, ESI-MS: 399[M+H]).

The synthesis of compound p: The compound o (10 mmol) was added in a 20 ml formic acid (80%) solution for reaction and the solution was stirred at a room temperature for 12 hours. After completion of the reaction, the solution was evaporated under a reduced pressure to remove the solvent. The residue and toluene were evaporated together to obtain a solid product. The obtained solid product was dissolved in the solution of dry pyridine and acetic anhydride for reaction at a room temperature for 4 hours. After the reaction was completed, the reaction solution was concentrated and then evaporated together with toluene to obtain the compound p (90.3%, ESI-MS: 427[M+H]). $^1$H NMR (CDCl$_3$, 300 MHz) δ: 2.07 (s, 3H), 2.85 (s, 1H), 4.62-4.77 (m, 2H), 4.89-5.07 (m, 3H), 7.32-8.17 (m, 10H).

The synthesis of compound q: The compound p (4.76 mmol) was dissolved in anhydrous dichloromethane (40 ml) and cooled to 0° C. The HCl gas was slowly introduced into the solution to saturation level for about 3 hours, and the solvent was removed through vacuum evaporation at a room temperature. The residue was dried in vacuum for 2 hours to obtain the compound q (yield=87.1%) which is directly applied in the next reaction.

The synthesis of compound r: With the existence of (NH$_4$)$_2$SO$_4$ (50 mg), 2,6-diamino-purine (4.78 mmol) and Hexamethyldisilazane (HMDS, 9 ml) were heated and refluxed to obtain transparent solution (in about 5 hours). The solvent was removed under vacuum to obtain a white solid product, and the solid product was dissolved in 1,2-dichloroethane (35 ml). Then, the 1,2-dichloroethane solution of compound q (4.56 mmol, 30 ml) and 0.4 nm molecular sieve (2.6 g) were added, and the solution was stirred for reaction at a room temperature for 6 days under nitrogen protection. After the reaction was detected by TLC as complete, the reaction solution was added with dichloromethane (80 ml) and filtered by diatomite. The filtrate was washed with saturated Na$_2$SO$_4$ and saline respectively. The organic layer was dried over anhydrous Na$_2$SO$_4$ overnight and the solvent was removed through evaporation to obtain the residue. The residue was separated under a reduced pressure by silica gel column, so as to obtain the compound r (yield=78.5%, ESI-MS: 517[M+H]). $^1$H NMR (CDCl$_3$, 300 MHz) δ: 2.85 (s, 1H), 4.67-4.79 (m, 2H), 4.92-5.13 (m, 3H), 5.79 (br, 1H), 7.32-8.17 (m, 9H), 8.35 (s, 1H). The synthesis of compound 25: The compound r (3.60 mmol) was dissolved in the saturated NH$_3$—CH$_3$OH solution (30 ml), and the solution was stirred for reaction at a room temperature for 15 hours. After completion of the reaction, the solvent was removed through evaporation and the residue was separated and purified by column chromatography to obtain the compound 25 (yield=78.9%, ESI-MS: 309 [M+H]). $^1$H NMR (CDCl$_3$, 300 MHz) δ: 2.85 (s, 1H), 3.69-3.79 (m, 2H), 4.79-5.07 (m, 3H), 5.60 (br, 1H), 5.79 (br, 1H), 7.32-8.17 m, 4H), 8.35 (s, 1H).

In Vitro Test on the Anti-HIV Activity of the Present Invention:

The anti-HIV activities of the compounds 1, 9, 15, 19, 36, 39, 46, 50 and 52 in the cell culture.

Drugs to be Tested:

The compounds 1, 9, 15, 19, 36, 39, 46, 50 and 52, no batch number, water-insoluble, DMSO-soluble. During the test, the solution was dissolved by DMSO to suitable concentration, diluted by culture medium, and immediately added into cell culture.

Positive Control Drugs:

(1) Zidovudine (AZT), a known HIV-1 nucleoside reverse transcriptase inhibitors that has been put into clinical application, in the form of white powder, purchased from Shanghai Desano Chemical & Pharmaceutical Co., Ltd., with batch number: 040201b;

(2) Nevirapine (NVP), one of known non-nucleoside reverse transcriptase inhibitors in clinical application, purchased from Nanjing Zezhong Medical & Chemical Information Research Center (Batch No: 0301001).

HIV-1IIIB Virus strain for test was donated by Dr. Jiang Jiandong, Mount Sinai Medical Center, USA, amplified in Cell H9 and under cryopreservation at −196° C.

Human T-lymphocyte subculture MT-4, donated by Professor Zhang Xingquan, Medical Research Center, University of Colorado (USA), subcultured in our laboratory, under cryopreservation at −196° C. Cell culture medium: RPMI Medium 1640 culture medium containing 10% fetal bovine serum, 100 IU/ml penicillin, 100 µg/ml streptomycin and kanamycin, and L-glutamine. The cells would be cultured at 37° C., in 5% CO$_2$ incubator, passaging once every three days.

Principal Reagents:

RPMI Medium 1640 culture medium, GIBCO (US); Fetal Bovine Serum (FBS), Tianjin Chuanye Biochemical Products Co., Ltd.; penicillin and streptomycin, North China Pharmaceutical Company; kanamycin, Shanghai Xudong Haipu Pharmaceutical Co., Ltd; tetrazolium (Thiazolyl blue, MTT) and citric acid, Sigma (U.S.); Triton X-100, KEBO AB STOCKHOLM (Sweden); N,N-dimethyl-Formamide, Beijing Chemical Plant; HIV-1 P24 antigen kit, BioMerieux (Netherlands).

Main Instruments:

Emax™ (Enzyme-labeled meter), MolICular Devices Inc. (United States);

Method:

With a 96-well culture plate, a test was conducted on the drug and the positive control drug group of drug-inhibited virus. Each well was added with 100 ul DMSO solution of different concentrations of the drugs or the positive control drugs AZT and NVP or oral drugs for rats, different doses of different groups, and then at different time blood sampling, and making different diluted group, 100 ul per well. At the same time, a test was conducted on cell control group, virus control group, positive drugs AZT and NVP control group. MT-4 cells were infected by 100TCID$_{50}$ HIV-1 IIIB for 1.5 hours, washed with medium once, and prepared to solution of $2 \times 10^5$ cells/ml that were inoculated in 96-well culture plates of the test groups of drug-inhibited virus, positive control drug group and virus control group. Cell control groups were added in equivalent medium and cultured for 4 days. Cytopathic changes were observed by microscopy, and toxicities were measured by MTT staining method. The P24 antigens in supernatant were measured according to the kits' instructions. Accordingly, the inhibition ratios, the median toxic concentrations (CC$_{50}$) and the median effective concentrations (IC$_{50}$) and SI were calculated respectively.

the Inhibition Effects of the Compounds 1, 9, 15, 19, 36, 39, 46, 50 and 52 on HIV-1 in MT-4 Cell Culture The cytotoxicities and anti-HIV-1 activities of the compounds 1, 9, 15, 19, 36, 39, 46, 50 and 52 were determined by MTT, and their cytotoxicities on CC$_{50}$ and SI were compared by using the HIV-1 infected and uninfected cells, as shown in Table 1.

TABLE 1

Anti-HIV-1 activities of the compound 1, 9, 15, 19, 36, 39, 46, 50, 52 and positive drugs AZT and NVP, in the MT-4 cell culture

| | CC$_{50}$(μg/ml)* | | | SI | |
|---|---|---|---|---|---|
| Drug | HIV-infected | HIV-uninfected | IC$_{50}$(μg/ml)* | HIV-infected | HIV-uninfected |
| AZT | >0.625 | >0.625 | 0.000182 | >3434 | >3434 |
| NVP | >12.5 | >12.5 | 0.00364 | >3434 | >3434 |
| 1 | 43.6 | 40.9 | 0.101 | 432 | 405 |
| 9 | 31.23 | 30.05 | 0.162 | 298 | 291 |
| 15 | >100 | >100 | 0.00001 | >100000 | >100000 |
| 19 | 43.8 | 39.8 | 0.09 | 487 | 422 |
| 36 | 35.12 | 37.54 | 0.127 | 276 | 296 |
| 39 | 38.26 | 36.77 | 1.49 | 26 | 25 |
| 46 | 48.52 | 55.35 | 0.131 | 370 | 423 |
| 50 | 28.3 | 27.9 | 2.30 | 12 | 12 |
| 52 | 41.3 | 38.6 | 0.133 | 311 | 290 |

*Cytotoxicity: MTT method

TABLE 2

The Pharmacological screening results of the compounds 1, 5 and 19 that were obtained by means of the pharmacological model of wild type HIV-1 replication

| Compound | Pharmacological model | cell | Administration Routine | Dose (mol/L) | Inhibition ratio (%) | solvent | Remarks IC$_{50}$ (μM) |
|---|---|---|---|---|---|---|---|
| 1 | VSVG/HIV-luc | Cell 293 | Proir to infection | $1 \times 10^{-5}$ | 99.4 ± 0.3 | DMSO | |
| | | | | $1 \times 10^{-6}$ | 90 ± 0 | DMSO | 0.5 μM |
| | | | | $1 \times 10^{-7}$ | 28 ± 0 | DMSO | |
| | | | | $1 \times 10^{-8}$ | 0 ± 3 | DMSO | |
| 15 | VSVG/HIV-luc | Cell 293 | Proir to infection | $1 \times 10^{-5}$ | 100 | DMSO | |
| | | | | $1 \times 10^{-6}$ | 100 | DMSO | 1.5 nM |
| | | | | $1 \times 10^{-7}$ | 100 | DMSO | |
| | | | | $1 \times 10^{-8}$ | 72 ± 6 | DMSO | |
| 19 | VSVG/HIV-luc | Cell 293 | Proir to infection | $1 \times 10^{-5}$ | 92.7 ± 0.9 | DMSO | |
| | | | | $1 \times 10^{-6}$ | 48 ± 0 | DMSO | 1.0 μM |
| | | | | $1 \times 10^{-7}$ | 4 ± 1 | DMSO | |
| | | | | $1 \times 10^{-8}$ | 0 ± 2 | DMSO | |
| AZT | VSVG/HIV-luc | Cell 293 | Proir to infection | $1 \times 10^{-7}$ | 97.2 ± 1.1 | DMSO | |
| | | | | $1 \times 10^{-8}$ | 54.1 ± 2.0 | DMSO | |
| 3TC | VSVG/HIV-luc | Cell 293 | Proir to infection | $1 \times 10^{-6}$ | 86.3 ± 4.3 | DMSO | |
| | | | | $1 \times 10^{-7}$ | 50.9 ± 2.4 | DMSO | |
| d4T | VSVG/HIV-luc | Cell 293 | Proir to infection | $1 \times 10^{-6}$ | 92.9 ± 1.6 | DMSO | |
| | | | | $1 \times 10^{-7}$ | 24.0 ± 1.1 | DMSO | |
| EFV | VSVG/HIV-luc | Cell 293 | Proir to infection | $1 \times 10^{-8}$ | 100 | DMSO | |
| | | | | $1 \times 10^{-9}$ | 55.2 ± 0.6 | DMSO | |
| NVP | VSVG/HIV-luc | Cell 293 | Proir to infection | $1 \times 10^{-7}$ | 73.1 ± 5.2 | DMSO | |
| | | | | $1 \times 10^{-8}$ | 18.8 ± 2.8 | DMSO | |

As can be known from Table 1 and Table 2, all the new 2'-fluoro-4'-substituted nucleosides have good anti-HIV activities, especially the compounds 1, 15 and 19 have good prospects in terms of application and development. Therefore, the development of such compounds will bring good news to patients with AIDS.

In Vitro Screening of Anti-Hepatitis B Virus Drugs in the Present Invention

Object:

HBV genome transfected Hep G2.2.15 cell is used for screening of anti-hepatitis B virus drugs to provide theoretical and experimental basis in research and development of novel anti-HBV drugs.

Method:

Lamivudine, compounds 15, 17 with concentration less than $TC_{50}$ were selected to treat cells. Cell culture supernatant was collected at the time point of 144 h and 216 h respectively, for fluorescent quantitative-PCR detection of HBV DNA levels.

Results:

Both Lamivudine and the compound 15 can significantly reduce the HBV DNA copy number after administration.

Conclusion:

The compound 15 can significantly reduce HBV DNA activity in vitro tests, with less toxicity. This experiment provided a basis for further study on anti-HBV effects of the compounds.

Cell Lines:

Hep G2.2.15 cell lines, the HBV DNA cloning transfected human liver cancer HepG2 developed by Mount Sinai Medical Center (United States) in 1986, characterized by the stable expressions of e antigen and surface antigen, donated by the Wuhan Institute of Virology, Chinese Academy of Sciences. Passage and G418 screening were made by our laboratory in the process of cell culture.

Test Drugs:

synthetic drugs of compound 15 and 17 in the present invention;

Control Drugs:

Lamivudine (3TC), GlaxoSmithKline, Suzhou, China.

Main Reagents and Instruments:

DMEM culture medium, Hyclone; FBS, Hangzhou Sijiqing; 24-well plates and culture bottles, Corning (USA); HBV PCR Fluorescence quantitative detection kit, Shenzhen PG Biotech; G418, Introvegen.

In Vitro Studies on Anti-HBV

Hep G2.2.15 cell culture: culture cell by DMEM medium containing 10% fetal bovine serum and 500 mg/L G418, digestion by 0.25% trypsin and 0.02% EDTA; 1:3 subculture; one passage every three days.

The Studies on the Anti-HBV Effects of Drugs:

The cells with good growth conditions were selected, and the cell concentration was adjusted to $2 \times 10^4$ cells/ml. Each well was inoculated by 1 ml in a 24-well plate. Then the cells were cultured at 37° C. in 5% $CO_2$ incubator for 48 hours. The test was started as soon as the cells have shown good adhesive growth. Grouping was made based on different concentrations of the drugs (Table 1). Each concentration was set for two wells. The cell culture control group without drug was set as a blank control. On the $3^{rd}$, $6^{th}$ and $9^{th}$ days after administration, the drug-containing medium and blank medium in the same concentration were renewed once, and the supernatant of each well was sucked into EP tube and stored at −20° C. for inspection.

TABLE 1

The concentrations of Lamivudine and the compounds 15 and 17

| Drug | concentration (μg/L) | | | | |
|---|---|---|---|---|---|
| Lamivudine (3TC) | 20,000 | 2000 | 200 | 20 | 2 |
| Compound 15 | 10 | 2 | 0.4 | 0.08 | 0.016 |
| Compound 17 | 1000 | 500 | 100 | | |

Fluorescence quantification detection on the drugs for HBV PCR:

the inhibition ratio of HBV DNA (%)=(HBV DNA copy numbers in the blank group−HBV DNA copy numbers in the test group)/HBV DNA copy numbers in the blank group×100%.

Results:

The inhibition effects of drugs on HBV DNA in Hep G2.2.15 cells supernatant are shown in Tables 2 and 3

TABLE 2

The effects of Lamivudine on the copy numbers of HBV DNA (copy numbers, x × $10^5$) in the cell supernatant

| Group | Concentartion (μg/ml) | HBV DNA Level | Inhibition ratio |
|---|---|---|---|
| Normal | / | 99.79 | / |
| 3TC | 20 μg/ml | 12.15 | 87.82 |
| | 2 μg/ml | 25.32 | 74.63 |
| | 0.21 μg/ml | 39.59 | 60.33 |
| | 0.02 μg/ml | 55.98 | 43.9 |

3TC $EC_{50}$ is 38.78 μg/L

TABLE 3

The effects of the compounds 15 and 17 on the copy numbers of HBV DNA (copy numbers, x × $10^5$) in the cell supernatant

| Group | Dose | HBV DNA copy number (*$10^5$) | Inhibition ratio (%) |
|---|---|---|---|
| Normal | / | 32.01 | / |
| 3TC | 10,000 μg/L | 5.49 | 82.8 |
| 15 | 2 μg/L | 5.21 | 83.7 |
| | 0.4 μg/L | 10.3 | 67.8 |
| | 0.08 μg/L | 13.5 | 57.8 |
| | 0.016 μg/L | 18.9 | 41.0 |
| 17 | 1000 μg/L | 10.2 | 67.9 |
| | 500 μg/L | 14.3 | 52.2 |
| | 100 μg/L | 19.2 | 40.6 |

For the compound 15, EC50 is 0.19 μg/L.

TABLE 4

The cytotoxicity of the compound 15 on Hep G2.2.15 (MTT)

| Group | Dose | OD Value | Cell Survival Rate |
|---|---|---|---|
| Normal | / | 0.644 | / |
| 15 | 1000 μg/ml | 0.520 | 82.6% |
| | 200 μg/ml | 0.552 | 85.5% |
| | 40 μg/ml | 0.606 | 96.7% |
| | 8 μg/ml | 0.626 | 98.7% |

In Vitro Test on the Anti-HCV Activity of the Present Invention

1. Materials and Methods

The HCV replication cells (Avva.5) were cultivated in the Dulbecco's improved Eagle medium containing 10% fetal calf serum and 1 mg/ml G418. 293-Sip-L cells were cultivated in the Dulbecco's improved Eagle medium containing 10% fetal calf serum, 250 μg/ml G418 and 150 μg/ml hygromycin B.

1.2 Method for Determining HCV Infection (RT-PCR Method)

Using Petri culture dish in a diameter of 60 mm, the cells were cultivated in a positive culture medium containing 100 μl of HCV for 12 hours. Then, the cells were cultivated in the fresh medium containing on HCV and the medium was replaced once everyday. When detecting HCV-RNA 7 days after the cells have been infected with HCV, it is necessary to clean the cells using the Dulbecco's improved Eagle medium in trypsinization and centrifugation methods. The upper layer part cleaned for the second time (used for comparison) and the washed cells were collected for RNA extraction and RT-PCR detection. β-actin mRNA was simultaneously determined for the purpose of comparison.

1.3 Quantitative Determination on HCV-RNA

The quantitative determination on HCV-RNA is performed in automatic PCR Enzyme-linked immunosorbent assay (ELISA). (Edition 2.0, Roche Diagnostics, Branchburg, N.J.)

2. Results

The compound 17 had inhibition effect when its concentration is 6 μg/ml, 0.6 μg/ml or 0.06 μg/ml (refer to the table below). HCV-NA level was determined in automatic PCR ELISA.

| The concentration of the compound 17 in the cell supernatant | Inhibition effect | |
|---|---|---|
| | Test 1 | Test 2 |
| 0 μg/ml | $5.1 \times 10^2$ | $4.4 \times 10^2$ |
| 0.06 μg/ml | $4.9 \times 10^2$ | $4.1 \times 10^2$ |
| 0.6 μg/ml | $0.92 \times 10^2$ | $0.78 \times 10^2$ |
| 6 μg/ml | $1.1 \times 10^2$ | $0.81 \times 10^2$ |

As shown in this table, the compound 17 had a relatively strong inhibition effect on HCV.

The invention claimed is:

1. A 2'-fluoro-4'-substituted nucleoside analogue of formula (I):

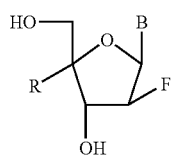

(I)

wherein:

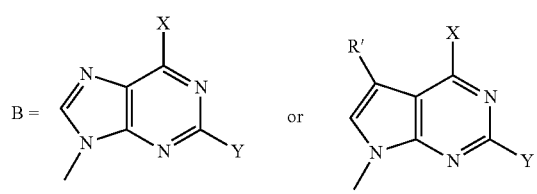

R = CH$_3$, CN, N$_3$, or C≡CH;
R' = H, or F;
X = F, OH, or NH$_2$;
Y = H, CH$_3$, F, OH, or NH$_2$ or wherein:

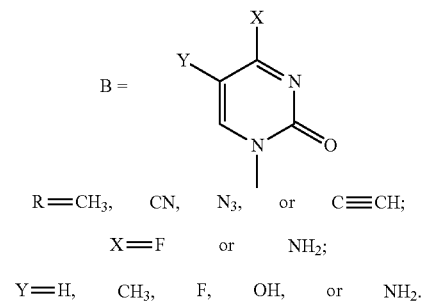

R=CH$_3$, CN, N$_3$, or C≡CH;

X=F or NH$_2$;

Y=H, CH$_3$, F, OH, or NH$_2$.

2. The 2'-fluoro-4'-substituted nucleoside analogue of claim 1, wherein, one or more salts are generated through a reaction between compounds of formula (I) and organic or inorganic acid.

3. The 2'-fluoro-4'-substituted nucleoside analogue of claim 1, wherein, said 2'-fluoro-4'-substituted nucleoside analogue is selected from the group consisting of the following:

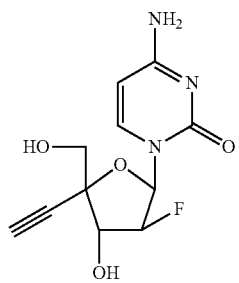

1

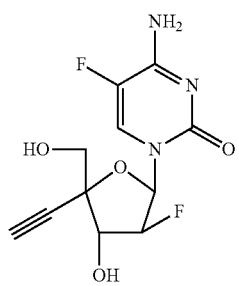

2

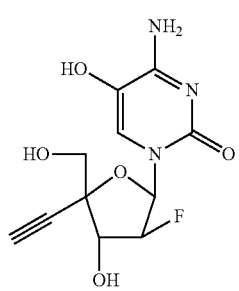

3

37
-continued
7
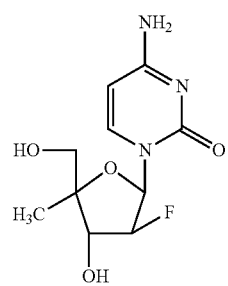
8
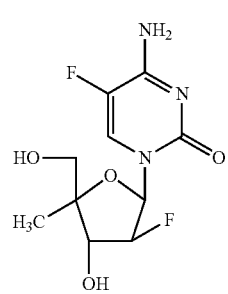
11
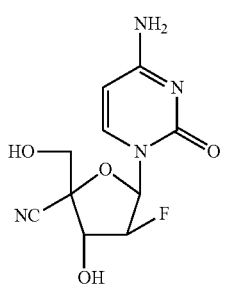
12
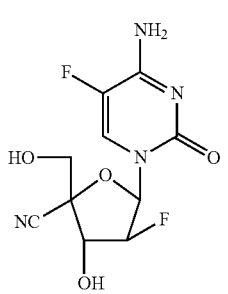
15
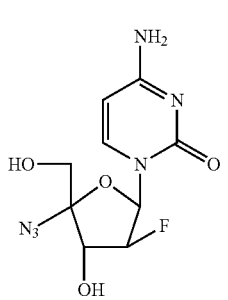
38
-continued
16
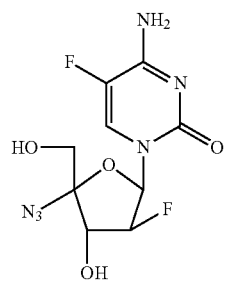
19
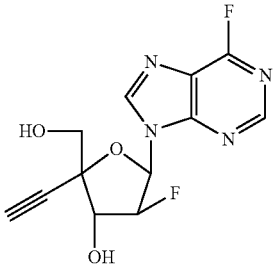
20
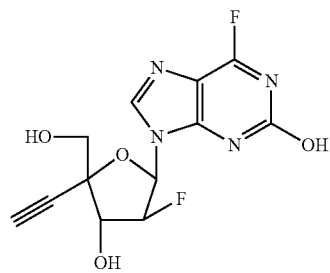
21
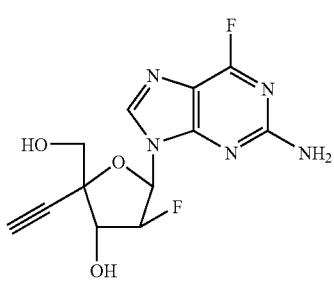
22
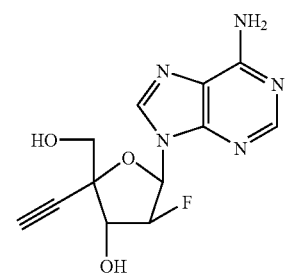
23
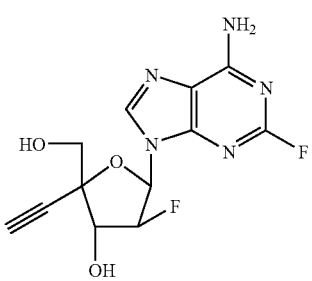

-continued
24
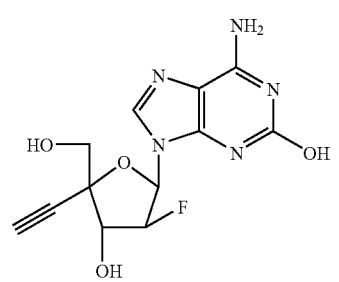
25
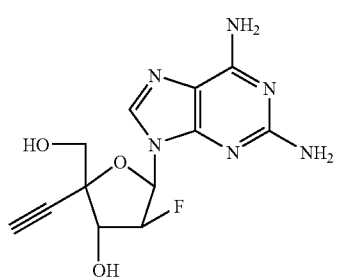
26
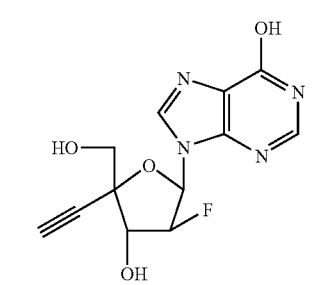
27
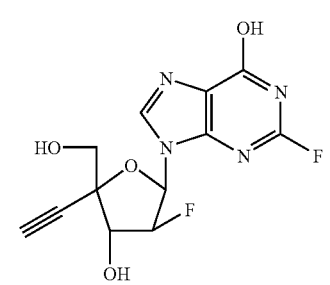
28
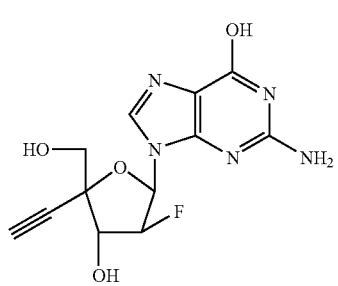
29
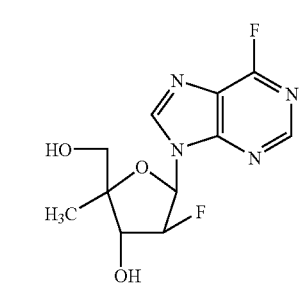
-continued
30
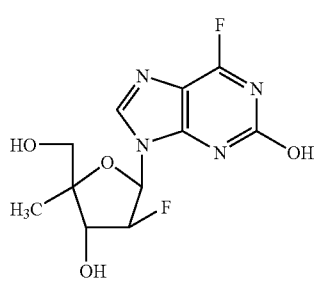
31
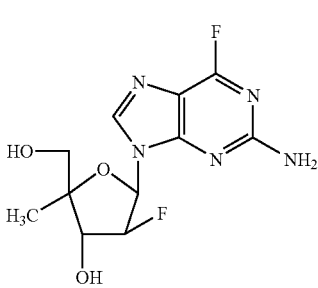
32
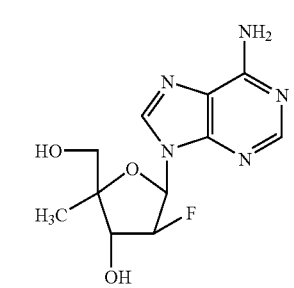
33
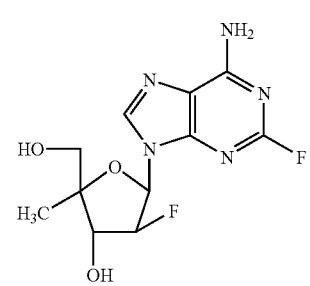
34
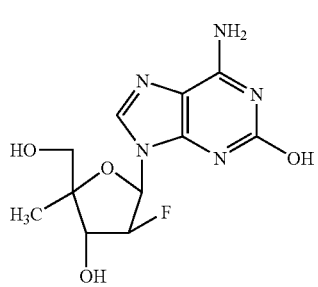
35
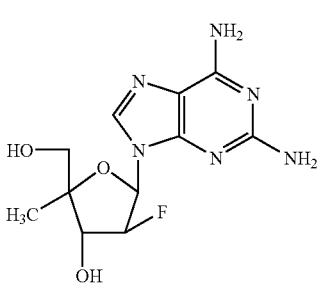

36
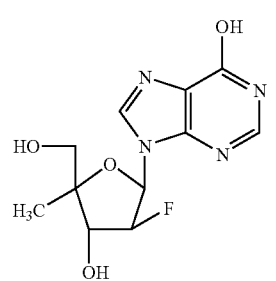
37
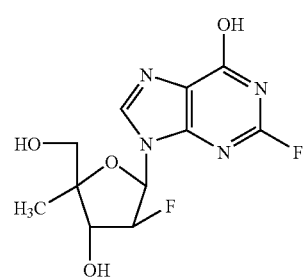
38
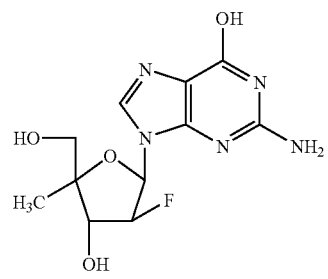
39
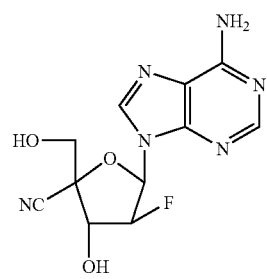
40
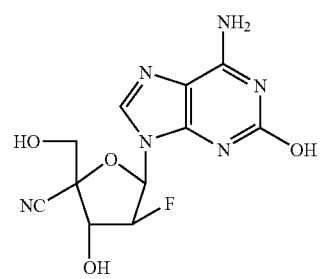
41
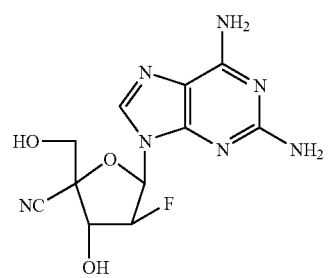
42
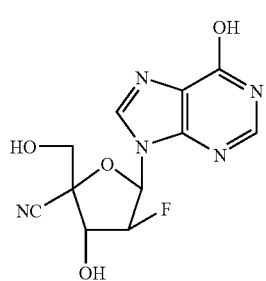
43
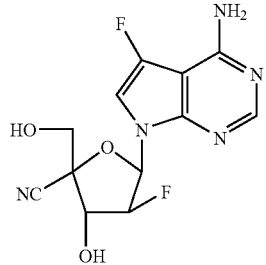
44
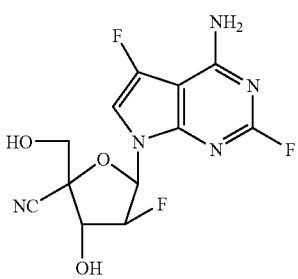
45
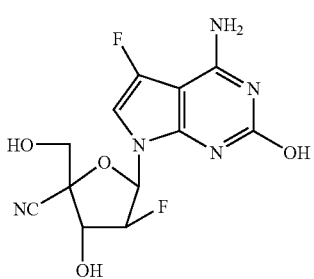
46
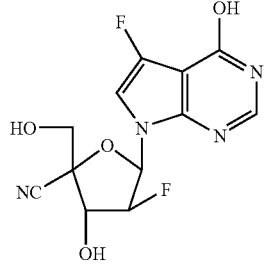
47
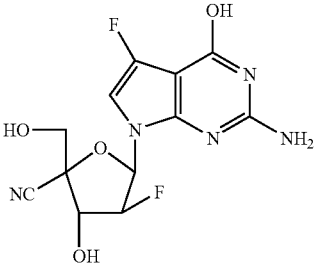

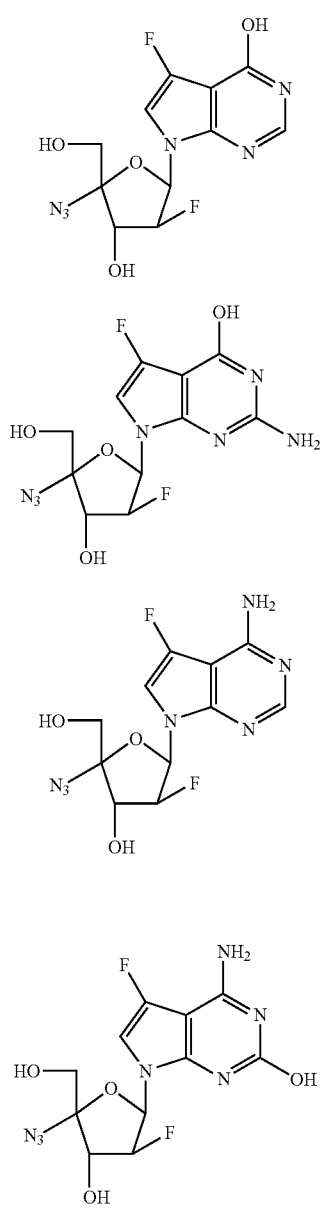
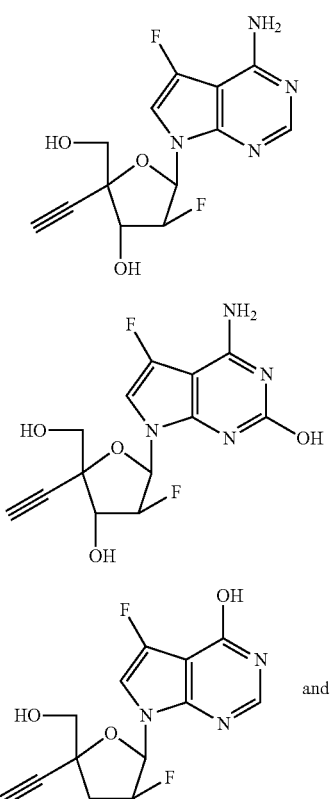
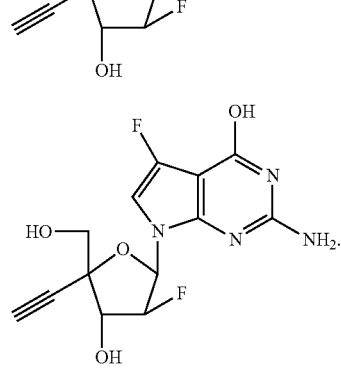
4. A method for the preparation of the nucleoside analogue of claim 1, characterized in that, said method comprises the steps of:
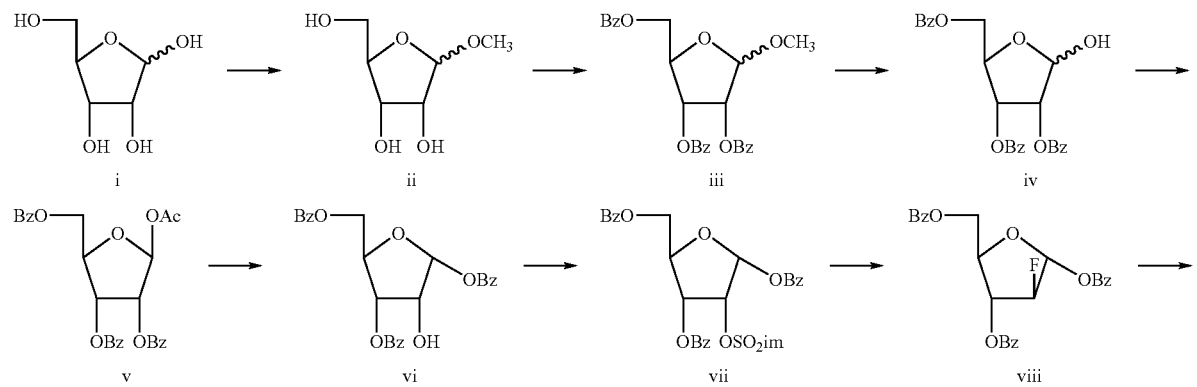

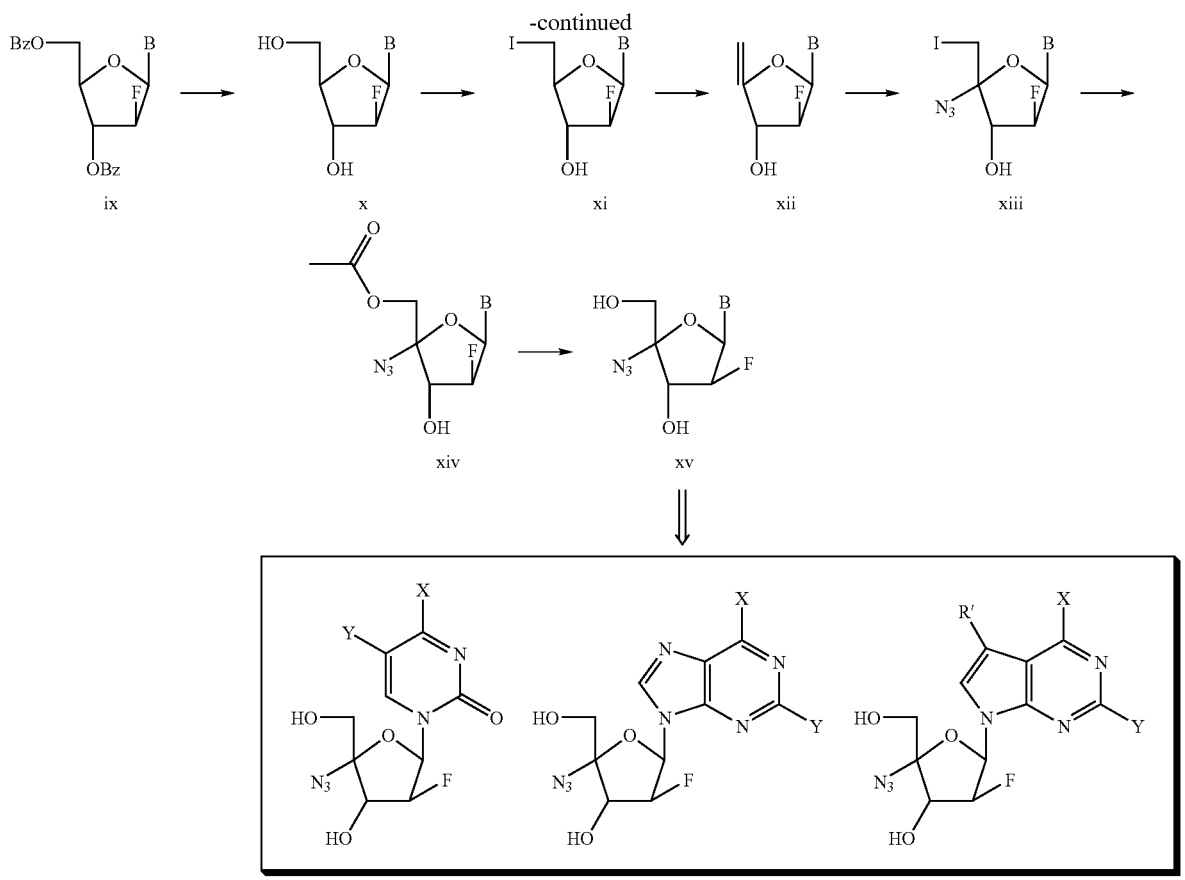

R' = H, F
X = F, OH, NH$_2$
Y = H, CH$_3$, F, OH, NH$_2$ the synthesis of compound ii: dissolving compound i (D-ribose or L-ribose) in HCl/MeOH, stirring in a water bath under hermetization and warm preservation, adding pyridine into the solution to terminate the reaction, and then drawing it off under a reduced pressure, so as to obtain light yellow syrup-like compound ii;

the synthesis of compound iii: dissolving the compound ii in dry pyridine, slowly adding benzoyl chloride dropwise in an ice-salt bath, stirring for reaction at a room temperature, pouring the reaction solution into ice-water after the reaction is completed, and extracting with chloroform; washing the organic layer sequentially with ice-water, pre-cooled sulfuric acid and saturated sodium bicarbonate until water layer shows weak alkaline, and then washing with ice-water until water layer shows neutral; drying the organic layer over anhydrous sodium sulfate, and then drawing it off under a reduced pressure, so as to obtain light yellow syrup-like compound iii;

the synthesis of compound iv: dissolving benzoyl compound iii in chloroform, adding red phosphorus, slowly adding bromine dropwise while stirring the solution in an ice-water bath, stirring for about 30 minutes, slowly adding ice water dropwise and stirring at a room temperature; then adding broken ice into the solution and stirring the solution until the ice is melted; subsequently pouring the reaction solution into ice water and extracting with chloroform; washing the organic layer with saturated sodium bicarbonate until the water layer shows weak alkaline, washing with ice-water until the water layer shows neutral, drying over anhydrous sodium sulfate, and then drawing it off under a reduced pressure to obtain dark yellow syrup; finally the syrup being separated by silica gel column, so as to obtain white dry syrup compound iv;

the synthesis of compound v: dissolving the compound iv in dry pyridine, slowly adding acetic anhydride dropwise in an ice water bath, and then stirring for about 30 minutes; removing the ice water bath, stirring at a room temperature for about 7 hours, and then the solution being heated up to 40° C. and kept for an hour; after adding broken ice and stirring it to be melted, pouring the reaction solution into ice water and extracting with chloroform; washing the organic layer sequentially with ice water, pre-cooled sulfuric acid and saturated sodium bicarbonate until the water layer shows weak alkaline, then washing with ice water until the water layer shows neutral, drying over anhydrous sodium sulfate, and then drawing it off under a reduced pressure, so as to obtain light yellow syrup-like compound v;

the synthesis of compound vi: dissolving the compound v in dry dichloromethane and slowly introducing the dry HCl gas into an ice-water bath, washing with ice-water so that an organic layer is separated; washing the organic layer with saturated sodium bicarbonate until the water layer shows weak alkaline, washing the organic layer with ice-water until the water layer shows neutral, drying over anhydrous sodium sulfate, and drawing it off under a reduced pressure to obtain light yellow syrup; recrystallizing the syrup to obtain white solid compound vi;

the synthesis of compound vii: dissolving the compound vi in dry dichloromethane and dry DMF, slowly adding SO₂Cl₂ into the solution with stirring at about −15° C. for about 30 minutes, naturally warming up to a room temperature for reaction; adding imidazole into the solution for three times at 0° C., and stirring the mixture at a room temperature, diluting the reaction solution by adding CH₂Cl₂ after the completion of the reaction, then washing the solution with ice water; extracting the water layer with CH₂Cl₂; combining the organic layers and then drying over anhydrous sodium sulfate, and drawing it off under a reduced pressure to obtain light yellow syrup; separating and purifying the syrup by silica gel column, so as to obtain white solid compound vii;

the synthesis of compound viii: dissolving the compound vii in ethyl acetate, and adding Et3N•3HF with stirring; heating up to about 60° C. with stirring for about 3 h, and then heating up to 70° C. with stirring for 1.5 h; adding ice-salt water to terminate the reaction, extracting with dichloromethane; combining the organic layers and then washing sequentially with saline, water and saturated sodium bicarbonate, drying over anhydrous sodium sulfate, and drawing it off under a reduced pressure to obtain dark yellow syrup; purifying the syrup to obtain light yellow syrup, and finally crystallizing the crude product to obtain the white crystalline compound viii;

the synthesis of compound ix: dissolving the compound viii in anhydrous dichloromethane, adding a mixed solution of HBr—AcOH, and stirring for reaction at a room temperature; after completion of the reaction, evaporating the mixture to dryness; dissolving the residue with dichloromethane, washing the dichloromethane solution with sodium bicarbonate solution, and removing dichloromethane through evaporation to obtain a syrup-like product; at the same time, the protected cytosine and (NH₄)₂SO₄ refluxing under nitrogen protection in the HMDS; after the completion of reaction, evaporating the solvent under a reduced pressure to obtain the silylated cytosine; dissolving the syrup obtained from the above reaction into dichloroethane, which is added into the silylated cytosine, and then refluxing for reaction under N₂ protection; adding ice to terminate the reaction; extracting with dichloromethane; and washing sequentially the dichloromethane layer with saturated sodium bicarbonate and saline, and drying over anhydrous sodium sulfate; evaporating the solvent to obtain white solid, separating and purifying by column chromatography to obtain the compound ix;

the synthesis of compound x: dissolving the compound ix in saturated NH₃—CH₃OH and stirring for reaction at a room temperature; after completion of the reaction, evaporating the solvent to dryness to obtain the residue; and purifying the residue by column chromatography to obtain the compound x;

the synthesis of compound xi: dissolving the compound x, imidazole and triphenylphosphine in tetrahydrofuran, slowly adding iodiferous tetrahydrofuran; stirring for reaction at a room temperature; removing the solvent through evaporation after completion of the reaction, adding ethyl acetate in the residue and filtering; evaporating ethyl acetate and separating the residue by column chromatography to obtain the compound xi;

the synthesis of compound xii: dissolving the compound ix in tetrahydrofuran and adding DBU; stirring for reaction at about 60° C.; evaporating the solvent to dryness after completion of the reaction; separating the residue by column chromatography to obtain the compound xii;

the synthesis of compound xiii: adding the DMF solution dissolved with ICl in the DMF solution dissolved with NaN₃ at 0° C.; stirring at the freezing point for about 10 minutes and slowly adding DMF dissolved with the compound xii to continue the reaction; a after completion of the reaction, adding sodium sulfite in the mixed solution until the color of iodine disappears completely; removing the solvent through evaporation under a reduced pressure; separating and purifying the residue by column chromatography, so as to obtain the compound xiii;

the synthesis of compound xiv: dissolving the compound xiii in DMF, and adding silver acetate with stirring; reacting at a room temperature; filtering after completion of the reaction; removing the solvent under a reduced pressure; purifying the residue by column chromatography, so as to obtain the compound xiv;

the synthesis of compound xv: dissolving the compound xiii in the solution of methanol-triethylamine, stirring for reaction at a room temperature; removing the solvent through evaporation after completion of the reaction, and purifying the residue by column chromatography, so as to obtain the compound xv.

5. A method for preparation of the nucleoside analogue of claim 1, characterized in that, said method comprises the follow steps:

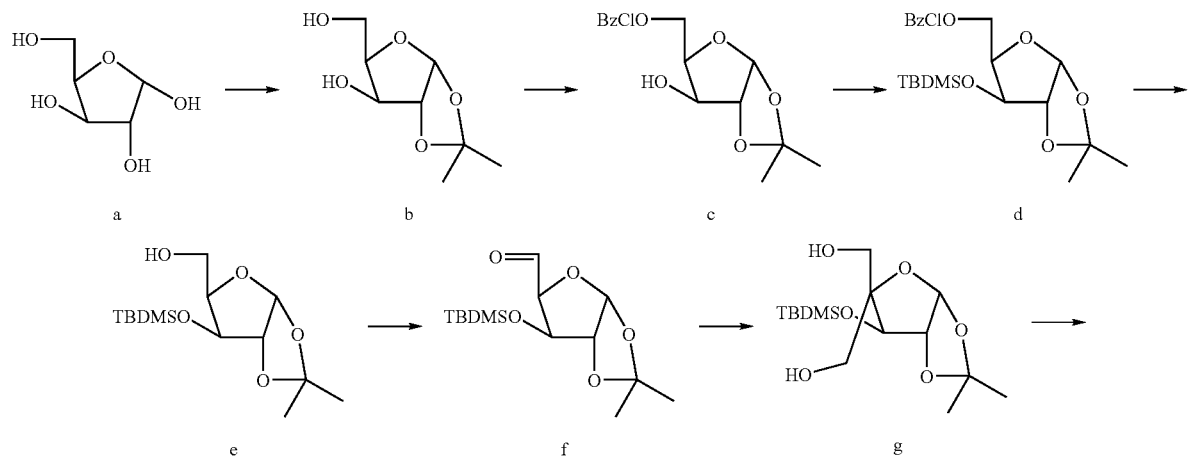

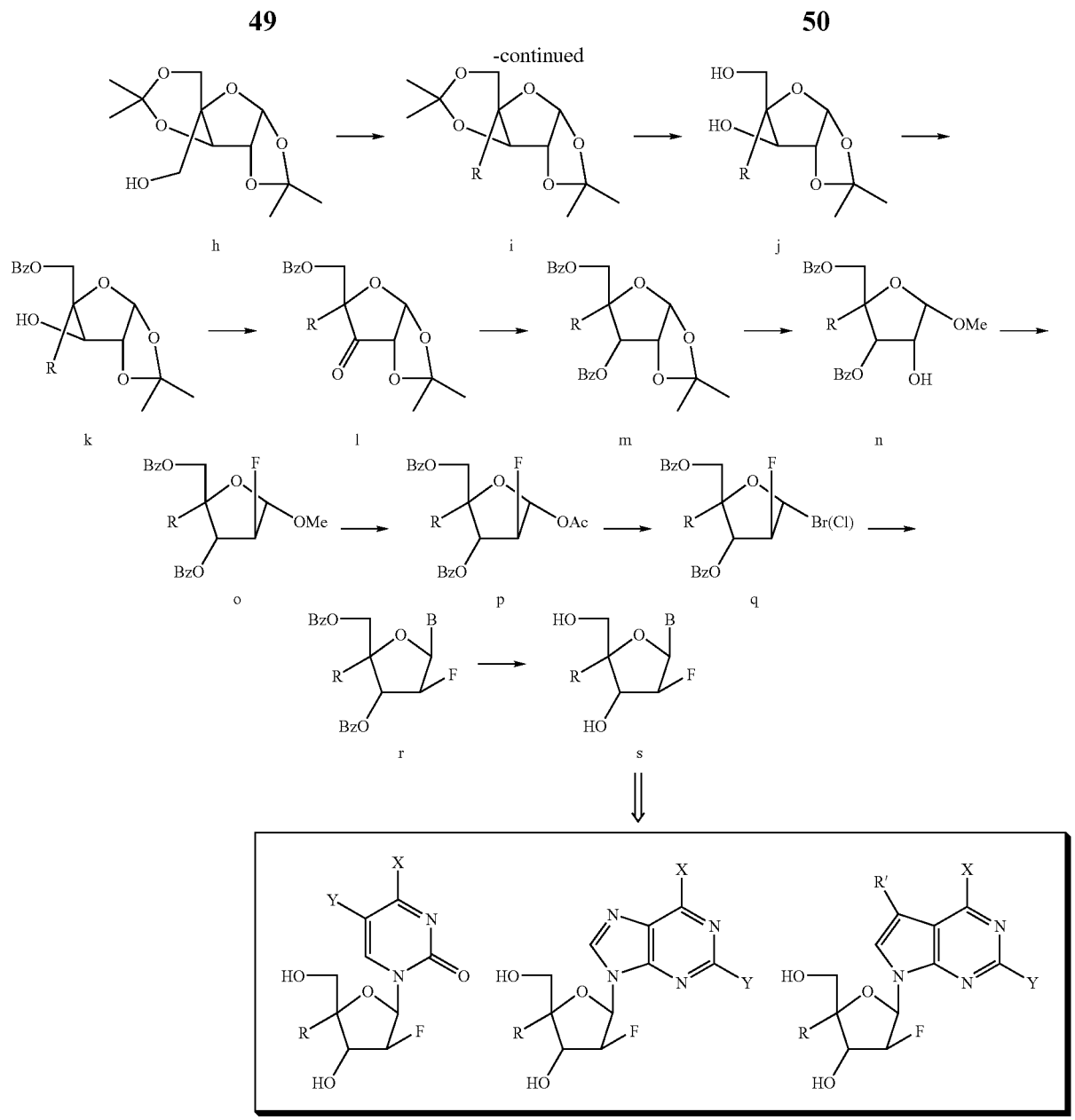

TBDMS = t-butyldimethylsilyl
R = CH₃, CN, —C≡CH
R' = H, F
X = F, OH, NH₂
Y = H, CH₃, F, OH, NH₂ the synthesis of compound b: adding compound a in acetone, slowly adding the concentrated sulfuric acid while stirring at a room temperature, and stirring for reaction at a room temperature; after the reaction is detected by TLC as complete, adding the concentrated ammonia to adjust pH=7~8, filtering and evaporating under a reduced pressure to remove most of the acetone; then adding 0.4% dilute hydrochloric acid with stirring, and reacting under the acetone reflux condition until the compound a has been completely hydrolyzed into the compound b; neutralizing the reaction solution by solid NaHCO₃, filtering, and evaporating to remove the solvent under a reduced pressure; dissolving the residue by dichloromethane, drying over anhydrous Na₂SO₄ for overnight, filtering, and then evaporating to remove the solvent, so as to obtain the yellow viscous oily compound b;

the synthesis of compound c: dissolving the compound b and triethylamine in dichloromethane; slowly adding dropwise parachlorobenzoyl chloride in an ice salt bath, and mechanically stirring for reaction at a temperature below 0° C.; after completion of the reaction, adding a saturated NaHCO₃ solution; washing the dichloromethane layer with water and saturated salt water, drying over anhydrous MgSO₄, filtering, and then evaporating under a reduced pressure to remove the solvent; recrystallizing the residue to obtain the white crystalline compound c;

the synthesis of compound d: dissolving the compound c in anhydrous dichloromethane; adding imidazole and tert-butyl-2-methyl chloride silicon (TBDMSCl) under nitrogen protection for the reaction at a room temperature; after completion of the reaction, neutralizing the reaction by hydrochloric acid, and obtaining two layers; washing the organic layer with water and saturated salt water respectively, drying over anhydrous $Na_2SO_4$, and then evaporating to remove the solvent; separating and purifying the residue by column chromatography, so as to obtain the compound d;

the synthesis of compound e: dissolving the compound xiii in the mixed solution of sodium methoxide and methanol for reaction at a room temperature; after completion of the reaction, neutralizing the solution by dilute acetic acid, filtering, washing with methanol and then evaporating under a reduced pressure to remove the solvent; finally separating and purifying the residue by column chromatography, so as to obtain the compound e;

the synthesis of compound f: adding dropwise DMSO into the dichloromethane solution of oxalyl chloride at about −60° C.; after stirring at the same temperature for about 15 minutes, adding dropwise the dichloromethane solution of the compound e; after stirring for reaction at about −65° C. for 30 minutes, adding triethylamine and stirring for the reaction at a room temperature; after completion of the reaction, adding water into the reaction solution so that an organic layer is separated; drying the organic layer over anhydrous magnesium sulfate, removing the solvent through evaporation; and separating and purifying the residue by column chromatography, so as to obtain the compound xiii;

the synthesis of compound g: adding sodium hydroxide and water in the reaction bottle; after stirring evenly, adding formaldehyde solution, 95% ethanol, and then the compound f, with stirring for reaction at about 35° C.; after completion of the reaction, cooling the reaction bottle with ice water while stirring until the product is completely precipitated; after the suction filtration, washing the solid product with water to neutral, drying, and dissolving it in anhydrous methanol, and then adding sodium borohydride for reflux reaction; after completion of the reaction, neutralizing the reaction solution by dilute hydrochloric acid and then extracting with dichloromethane, drying over anhydrous $Na_2SO_4$, and removing the solvent, so as to obtain the compound g;

the synthesis of compound h: dissolving the compound g in methanol, and adding Dowex $H^+$ (washed with methanol in advance) for reaction at a room temperature; after completion of the reaction, removing the resin from the solution through filtration and repeatedly washing it with methanol, and evaporating the solution to obtain the solid substance; dissolving the obtained solid substance in acetone, then slowly adding concentrated sulfuric acid (a catalytic amount) into the solution for reaction at a room temperature while stirring; adding concentrated ammonia water to adjust pH value, and then filtering and evaporating under a reduced pressure to remove acetone, so as to obtain the compound h;

the synthesis of compound i: adding dropwise DMSO into the dichloromethane solution of oxalyl chloride at about −60° C., and stirring for about 15 minutes after dripping off; adding dropwise the dichloromethane solution of the compound h, reacting for about 30 minutes at −60° C. after dripping off; adding triethylamine in the solution; after the reaction is carried out at a room temperature for about 30 minutes, adding water to terminate the reaction; separating the organic layer and drying over anhydrous $Na_2SO_4$; removing the solvent through evaporation and separating and purifying the residue by column chromatography to obtain the solid product; adding $ClCH_2P(C_6H_5)_3Cl$ into anhydrous tetrahydrofuran, cooling to about −78° C., adding n-BuLi hexane solution, and stirring for reaction for about an hour; then adding the dry tetrahydrofuran solution of the solid product; increasing the temperature of the solution gradually to about 0° C. to continue the reaction; after completion of the reaction, adding a saturated $NH_4Cl$ solution carefully dropwise in the solution, and subsequently extracting with ethyl acetate; washing the organic layer with saline twice, drying over anhydrous $MgSO_4$, and evaporating to remove the solvent; dissolving the residue obtained into anhydrous tetrahydrofuran, cooling to −78° C., and slowly adding dropwise n-BuLi hexane solution; after stirring the solution for 2 hours, terminating the reaction carefully by using saturated $NH_4Cl$; washing the organic layer with saturated salt water, drying over anhydrous MgSO4, and evaporating under a reduced pressure to remove the solvent; finally separating and purifying the residue by rapid silica gel column, so as to obtain the compound i;

the synthesis of compound j: adding the compound i in the diluted hydrochloric acid solution, stirring the solution at a room temperature for reaction; after completion of the reaction, neutralizing the solution with solid $NaHCO_3$, and then filtering; evaporating the filtrate under a reduced pressure to remove the solvent; dissolving the residue in dichloromethane; filtering after drying over anhydrous $Na_2SO_4$, and evaporating to remove the solvent, so as to obtain the compound j;

the synthesis of compound k: dissolving the compound j in pyridine, adding BzCl dropwise for reaction at a room temperature; after completion of the reaction, evaporating the solvent to dryness, and purifying the residue to obtain the compound k;

the synthesis of compound l: dissolving the compound k and 2,2,6,6-tetramethyl piperidine-N-oxide in dichloromethane, cooling to 0° C. and adding the mixed solution of sodium hypochlorite solution, $NaHCO_3$ and water in the reaction solution for reaction at 0° C. for about 30 minutes; adding isopropanol and stirring at a room temperature; washing the separated dichloromethane layer with water twice, drying over anhydrous $MgSO_4$, filtering, and evaporating to remove the solvent; recystalizing the residue to obtain the compound l;

the synthesis of compound m: dissolving the compound l in the mixed solution of absolute ethanol and ethyl acetate and cooling to about 0° C.; adding sodium borohydride in batches and stirring for reaction; after completion of the reaction, neutralizing with dilute acetic acid solution, filtering, and evaporating the filtrate to dryness; dissolving the residue in dichloromethane and then washing with water; drying the dichloromethane layer over anhydrous $MgSO_4$, filtering, and evaporating to remove the dichloromethane under a reduced pressure; recrystallizing the residue by the mixed solvent of dichloromethane and petroleum ether to obtain solid substance; then dissolving the solid product in pyridine, and adding dropwise BzCl at about 0° C.; after that, the reaction is carried out at a room temperature; after completion of the reaction, removing the solvent through evaporation and extracting the residue with ethyl acetate, washing with saturated NaHCO₃ solution, drying over anhydrous Na₂SO₄, filtering, and evaporating to remove the solvent, so as to obtain the compound m;

the synthesis of compound n: dissolving the compound m in methanol, adding the mixed solution of concentrated hydrochloric acid/dioxane for reaction at a room temperature; after completion of the reaction, neutralizing the reaction solution with NaHCO₃, and filtering; removing the solvent from the filtrate by vacuum distillation; dissolving the residue in appropriate amount of dichloromethane, drying over anhydrous Na₂SO₄ for overnight, filtering, and evaporating to dryness; separating and purifying by column chromatography to obtain the compound n;

the synthesis of compound o: dissolving the compound n in dichloromethane, and adding DAST under a room temperature and stirring for reaction; after completion of the reaction, pouring the mixture into the saturated NaHCO₃ solution and separating the organic layer; washing the organic layer with the saturated NaHCO₃ solution, drying over anhydrous Na₂SO₄, and separating and purifying by column chromatography to obtain the compound o;

the synthesis of compound p: dissolving the compound o in formic acid solution, and stirring at a room temperature for reaction; after completion of the reaction, removing the solvent under a reduced pressure; evaporating the residue and toluene together to obtain the solid product; dissolving the obtained a solid product in the solution of dry pyridine and acetic anhydride for reaction at a room temperature; after the reaction is completed, concentrating the reaction solution and then evaporating together with toluene, so as to obtain the compound p;

the synthesis of compound q: dissolving the compound p in anhydrous dichloromethane and cooling to 0° C.; slowly introducing the HCl gas into the solution to a saturation level and removing the solvent by vacuum evaporation at a room temperature; drying the residue in vacuum to obtain the compound q;

the synthesis of compound r: with the existence of (NH₄)₂SO₄, refluxing 2,6-diamino-purine and Hexamethyldisilazane (HMDS) to be a transparent solution; removing the solvent under vacuum to obtain a white solid product, and dissolving the solid product in 1,2-dichloroethane; adding 1,2-dichloroethane solution of compound q and molecular sieve, and stirring for reaction under nitrogen protection at a room temperature; after the reaction is detected by TLC as complete, adding dichloromethane in the reaction solution and filtering by diatomite; washing the filtrate with saturated Na₂SO₄ and saline respectively; drying the organic layer over anhydrous Na₂SO₄ overnight and removing the solvent through evaporation to obtain the residue; separating the residue under a reduced pressure through silica gel column, so as to obtain the compound r;

the synthesis of compound s: dissolving the compound r in a saturated NH₃—CH₃OH solution, and stirring for reaction at a room temperature; after completion of the reaction, removing the solvent through evaporation and separating and purifying the residue by column chromatography, so as to obtain the compound s.

6. The 2'-fluoro-4'-substituted nucleoside analogue of claim 1, further comprising esters or salts of the 2'-fluoro-4'-substituted nucleoside analogue, wherein the salts are generated through the reaction between active compounds (I) and organic or inorganic acid.

7. The 2'-fluoro-4'-substituted nucleoside analogue of claim 1, further comprising salts generated through a reaction between the compounds of formula (I) or pro-drugs thereof or 5'-phosphate esters thereof and organic or inorganic acid.

8. The 2'-fluoro-4'-substituted nucleoside analogue of claim 1, further comprising 5'-phosphate esters of the 2'-fluoro-4'-substituted nucleoside analogue of formula (I).

9. The 2'-fluoro-4'-substituted nucleoside analogue of claim 8, wherein the 5'-phosphate esters of the 2'-fluoro-4'-substituted nucleoside analogue of formula (I) exist as salts generated through a reaction between the 5'-phosphate esters of formula (I) and an organic or inorganic acid.

10. A 2'-fluoro-4'-substituted nucleic acid base analogue of formula (I):

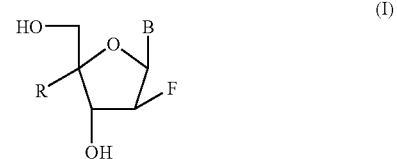

wherein:

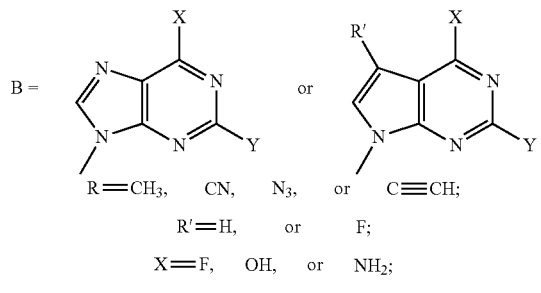

R=CH₃, CN, N₃, or C≡CH;
R'=H, or F;
X=F, OH, or NH₂;
Y=H, CH₃, F, OH, or NH₂ or
wherein:

B =

R=CH₃, CN, N₃, or C≡CH;
X=F, or NH₂;
Y=H, CH₃, F, OH, or NH₂ or 5'-phosphate esters of the 2'-fluoro-4'-substituted nucleic acid base analogue of formula (I);

or salts of the 2'-fluoro-4'-substituted nucleic acid base analogue of formula (I) or the 5'-phosphate esters thereof, wherein the salts are generated through a reaction between compounds of formula (I) or the 5'-phosphate esters thereof and organic or inorganic acid.

11. The 2'-fluoro-4'-substituted nucleic acid base analogue of claim 10, wherein, said 2'-fluoro-4'-substituted nucleoside analogue is selected from the group consisting of the following:

1
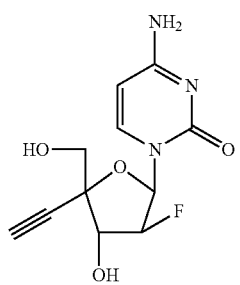
2
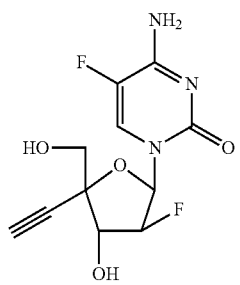
3
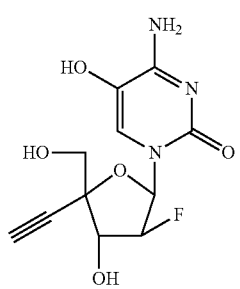
7
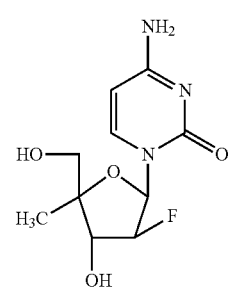
8
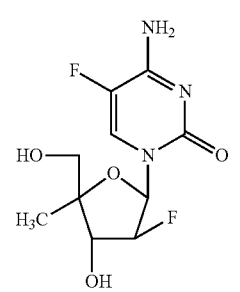
11
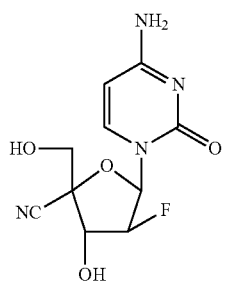
12
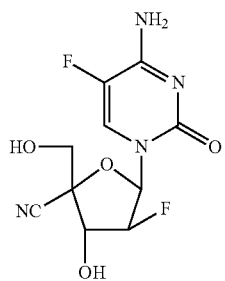
15
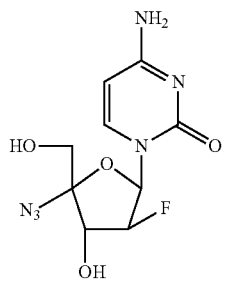
16
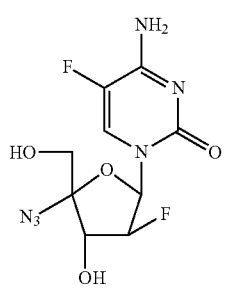
19
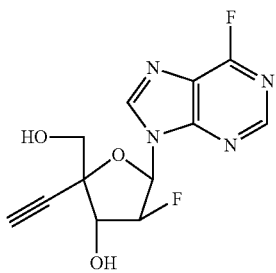

20 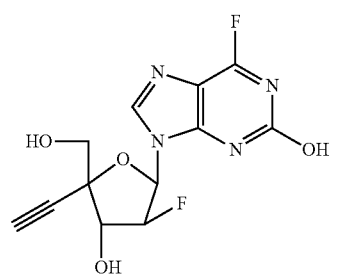
21 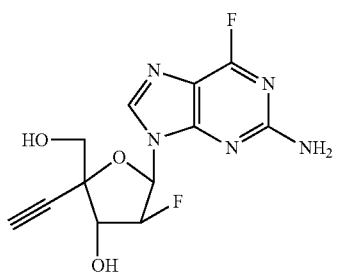
22 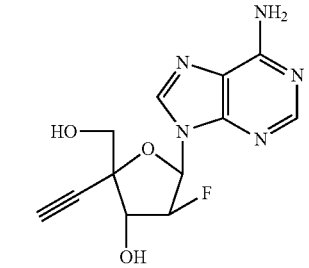
23 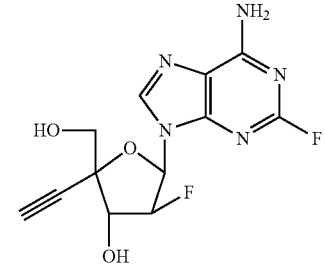
24 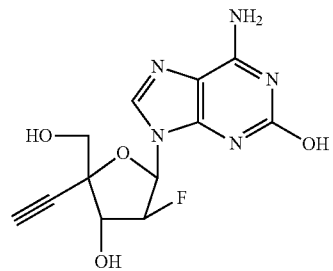
25 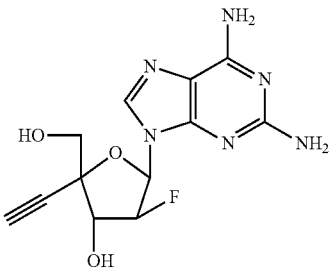
26 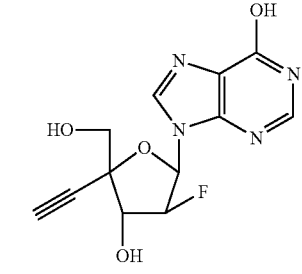
27 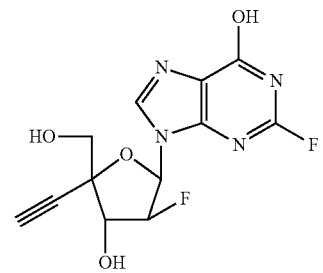
28 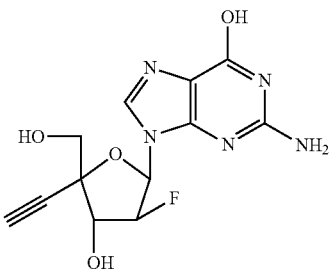
29 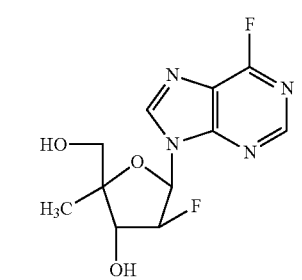

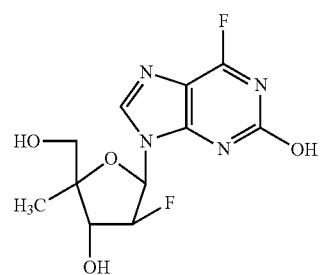
30
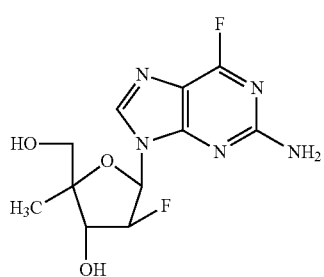
31
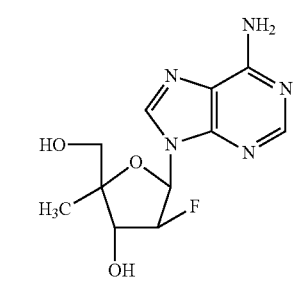
32
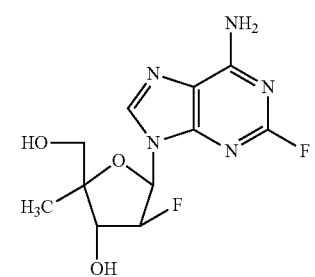
33
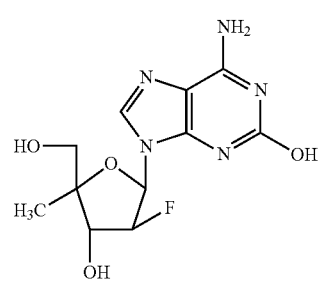
34
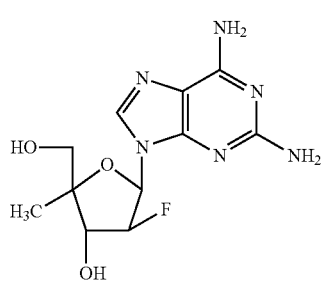
35
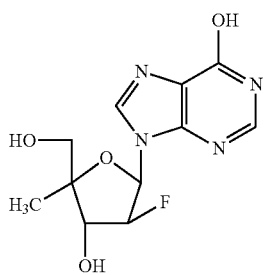
36
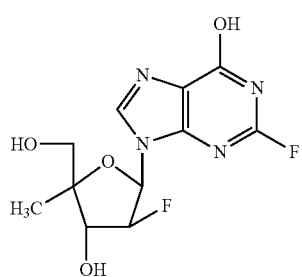
37
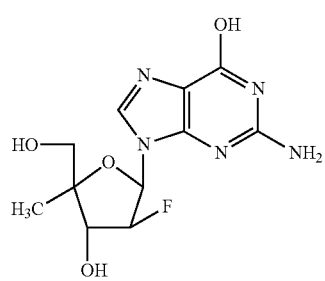
38
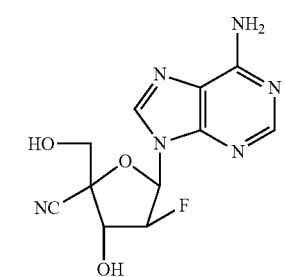
39
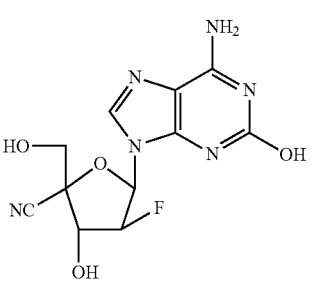
40
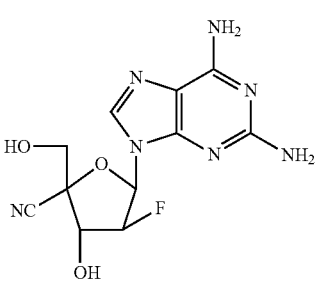
41

42
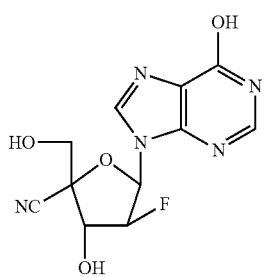
43
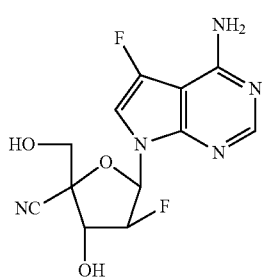
44
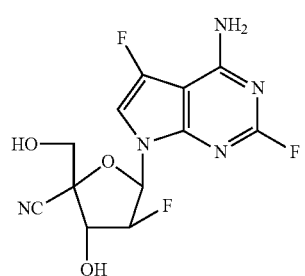
45
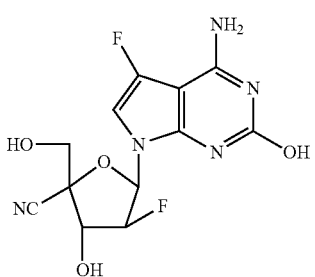
46
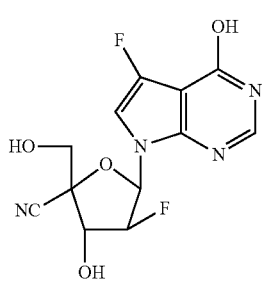
47
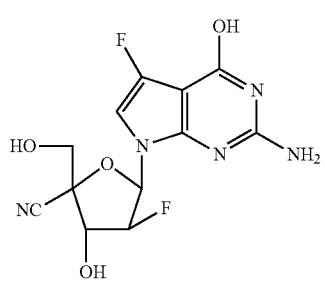
48
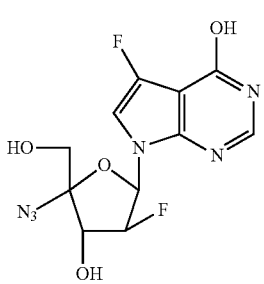
49
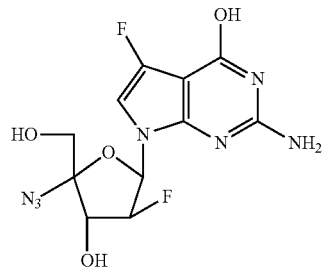
50
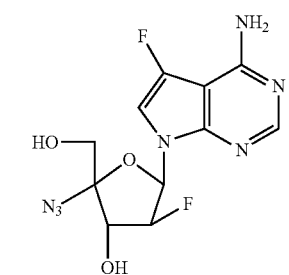
51
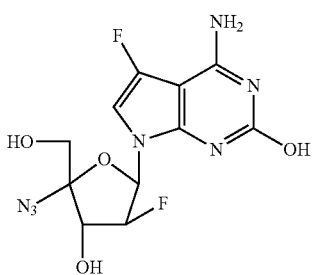
52

-continued

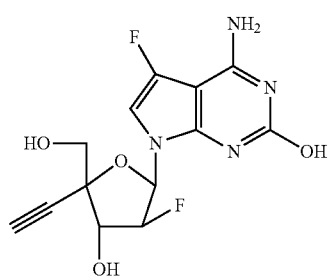

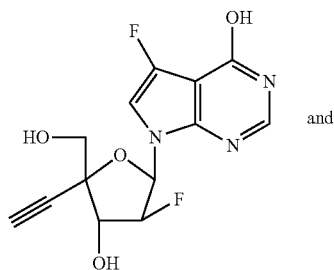

and

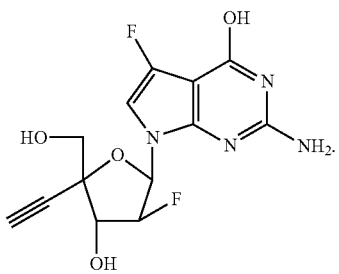

12. The 2'-fluoro-4'-substituted nucleic acid base analogue of claim 10, wherein, said 2'-fluoro-4'-substituted nucleoside analogue is selected from the group consisting of the following compounds:

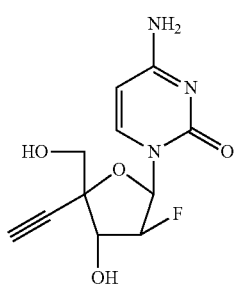

1

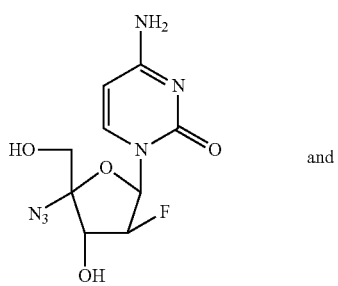

and

-continued

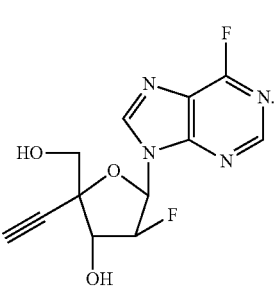

19

13. The 2'-fluoro-4'-substituted nucleoside analogue of claim 1, characterized in that, said 2'-fluoro-4'-substituted nucleoside analogue is selected from the group consisting of the following compounds:

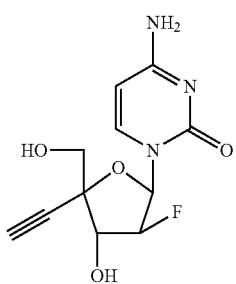

1

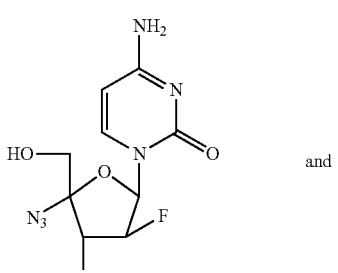

15 and

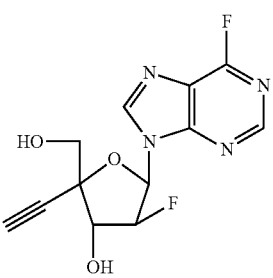

19

\* \* \* \* \*